US008211642B2

(12) United States Patent
Hussey et al.

(10) Patent No.: US 8,211,642 B2
(45) Date of Patent: Jul. 3, 2012

(54) COMPARATIVE GENOMIC HYBRIDIZATION

(75) Inventors: Nicole Dominique Hussey, West Beach (AU); Dong Gui Hu, Fulham Gardens (AU)

(73) Assignee: Adelaide Research & Innovation Pty Ltd, Adelaide (AU)

( * ) Notice: Subject to any disclaimer, the term of this patent is extended or adjusted under 35 U.S.C. 154(b) by 1276 days.

(21) Appl. No.: 10/551,150

(22) PCT Filed: Apr. 2, 2004

(86) PCT No.: PCT/AU2004/000429
§ 371 (c)(1),
(2), (4) Date: Nov. 17, 2006

(87) PCT Pub. No.: WO2004/088310
PCT Pub. Date: Oct. 14, 2004

(65) Prior Publication Data
US 2007/0160988 A1  Jul. 12, 2007

(30) Foreign Application Priority Data
Apr. 2, 2003 (AU) ................................ 2003901671

(51) Int. Cl.
C12Q 1/68 (2006.01)
C12P 19/34 (2006.01)
C07H 21/04 (2006.01)

(52) U.S. Cl. ..................... 435/6.12; 435/91.2; 536/23.1; 536/24.33

(58) Field of Classification Search ............. 435/6, 91.2; 536/24.31, 24.32, 24.33
See application file for complete search history.

(56) References Cited

U.S. PATENT DOCUMENTS
6,432,650 B1  8/2002  Christian et al.

FOREIGN PATENT DOCUMENTS
| WO | WO-00/12675 A1 | 3/2000 |
| WO | WO-00/24925 A1 | 5/2000 |
| WO | WO 0024925 A1 * | 5/2000 |
| WO | WO-01/29252 A2 | 4/2001 |
| WO | WO-03/027638 A1 | 4/2003 |

OTHER PUBLICATIONS

Fiegler, H. et al. DNA microarrays for comparative genomic hybridization based on DOP-PCR amplification of BAC and PAC clones. Genes, Chrososmes, & Cancer, vol. 36, pp. 361-374, Apr. 2003, published online Jan. 27, 2003.*
Fiegler, H. et al., Genes Chromosomes Cancer, Apr. 2003, Published online Jan. 27, 2003, 36(4): 361-74.
Martinez-Ramirez, A., et al., Cancer Genetics and Cytogenetics (2003), 144(1): 87-89.
Sudbark, R. et al., Human Molecular Genetics (2001), 10(1): 77-83.
Voullaire, L. et al., Prenatal Diagnosis, Sep. 19, 1999 (9): 846-51.
Solinas-Toldo, S. et al., Genes Chromosomes Cancer; Dec. 20, 1997 (4): 399-407.
Hu, Dg et al., Molecular Human Reproduction, Apr. 10, 2004, (4): 283-9.
Bolzer et al., "A complete set of repeat-depleted, PCR-amplifiable, human chromosome-specific painting probes," Cytogenetics and Cell Genetics, vol. 84, pp. 233-240 (1999).
Wang et al., "COT-1 Banding of Human Chromosomes Using Fluorescence In Situ Hybridization With CY3 Labeling." Jpn. J. Human Genetics, vol. 40, No. 3, pp. 243-252, 1995.
Buzek et al., "Isolation and characterization of X chromosome-deprived DNA sequences from a dioecious plant *Melandrium album*," Chromosome Research, vol. 5, No. 1, pp. 57-65, 1997.
Franke et al; American Journal of Pathology, vol. 161, No. 5, pp. 1861-1867, Nov. 2002.
Nancy Wang; American Journal of Medical Genetics (Semin. Med. Genet.), vol. 115, No. 3, pp. 118-124, (2002).
B. Beheshti et al; Cancer Genetics and Cytogenetics, vol. 137, No. 1, pp. 15-22, (2002).
Makrigiorgos et al; Nature biotechnology, vol. 20, No. 9, pp. 936-939, Sep. 2002.
Harada et al; Oncology, vol. 62, No. 3, pp. 251-258, 2002.
Daigo et al; American Journal of Pathology, vol. 158, No. 5, pp. 1623-1631, May 2001.
Eugene Pergament; Bailliere's Clinical Obstetrics and Gynaecology, vol. 14, No. 4, pp. 677-690, 2000.
Jung et al; Journal of Neuropathology and Experimental Neurology, vol. 58, No. 9, pp. 993-999, Sep. 1999.
Alcock et al; Journal of Clinical Pathology—Molecular Pathology, vol. 52, No. 3, pp. 160-163. (1999).
Zitzelsberger et al; Virchows Archiv, vol. 433, No. 4, pp. 297-304, 1998.
Weber et al; American Journal of Pathology, vol. 153, No. 1, pp. 295-303, Jul. 1998.

* cited by examiner

*Primary Examiner* — Prabha Chunduru
(74) *Attorney, Agent, or Firm* — Birch, Stewart, Kolasch & Birch, LLP

(57) ABSTRACT

The present invention relates to a method of comparing at least one chromosome or part thereof from a cell with a first karyotype with the corresponding chromosome or part thereof from a cell with a second karyotype. The method includes the steps of: (a) amplifying DNA from an isolated chromosome or part of an isolated chromosome; (b) attaching the amplified DNA to a solid substrate; (c) amplifying DNA from one or more cells with a first karyotype and amplifying DNA from one or more cells with a second karyotype; (d) labelling the amplified DNA from the one or more cells with a first karyotype with a first label, and labelling the amplified DNA from the one or more cells with a second karyotype with a second label, wherein the first and second labels are detectably different; (e) hybridizing the amplified and labelled DNA from the one or more cells with a first karyotype to the amplified DNA attached to the solid substrate, and hybridizing the amplified and labelled DNA from the one or more cells with a second karyotype to the amplified DNA attached to the solid substrate; and (f) comparing the relative amount of first and second labels hybridized to the amplified DNA attached to the solid substrate.

7 Claims, 15 Drawing Sheets

DYS: 19 385 437 439

389 390 393

M₁ M₂ 19 385 389 390 -

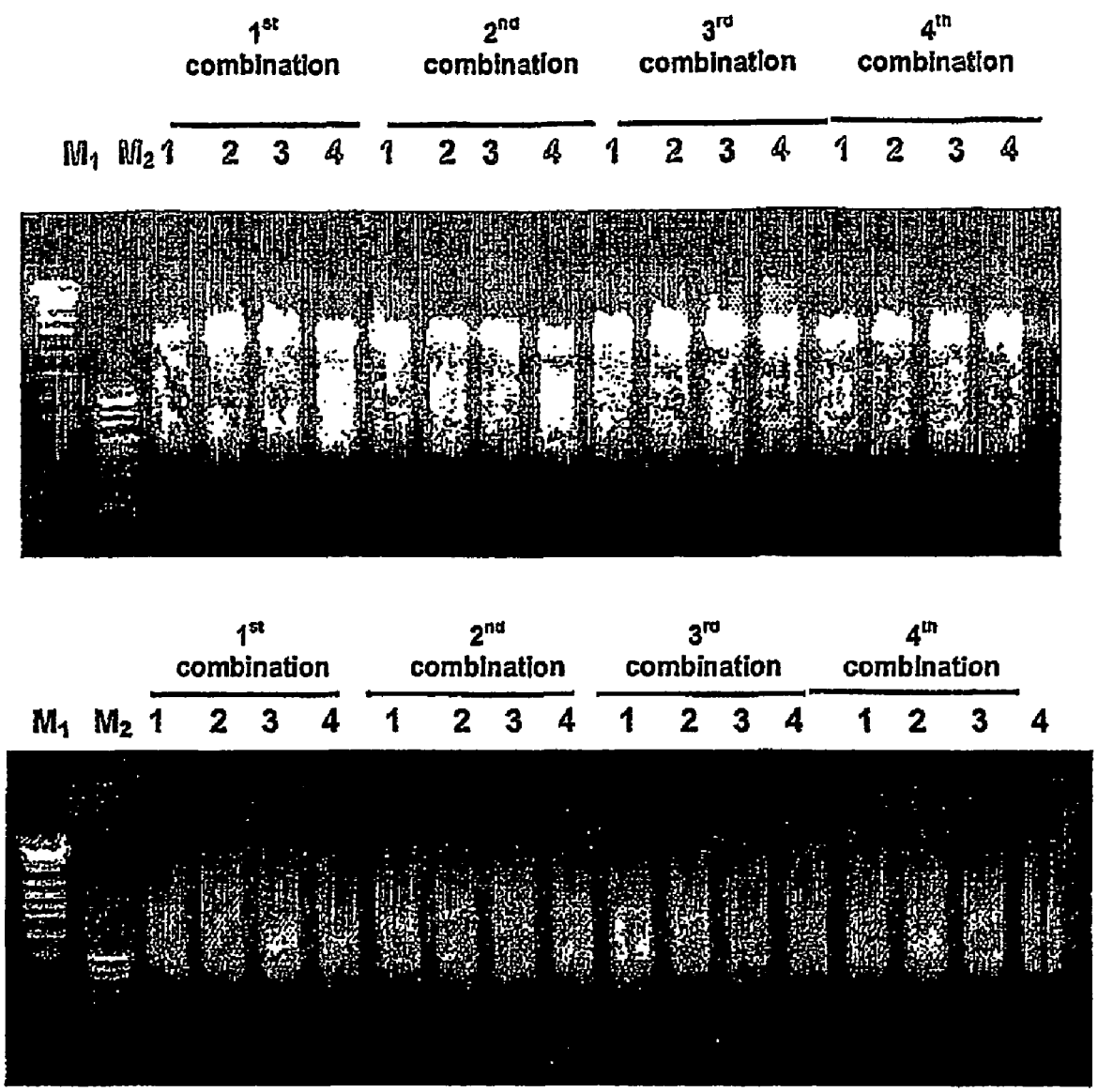

SEQUENCE LISTING

<160> NUMBER OF SEQ ID NOS: 25

<210> SEQ ID NO 1
<211> LENGTH: 22
<212> TYPE: DNA
<213> ORGANISM: Artificial Sequence

```
<220> FEATURE:
<223> OTHER INFORMATION: DOP
<220> FEATURE:
<221> NAME/KEY: misc_feature
<222> LOCATION: (11)..(16)
<223> OTHER INFORMATION: n is a, c, g, or t

<400> SEQUENCE: 1
ccgactcgag nnnnnnatgt gg                                                  22

<210> SEQ ID NO 2
<211> LENGTH: 24
<212> TYPE: DNA
<213> ORGANISM: Artificial Sequence
<220> FEATURE:
<223> OTHER INFORMATION: primer sequence

<400> SEQUENCE: 2
tgaaataatg gagatgcaat gttc                                                24

<210> SEQ ID NO 3
<211> LENGTH: 24
<212> TYPE: DNA
<213> ORGANISM: Artificial Sequence
<220> FEATURE:
<223> OTHER INFORMATION: primer sequence

<400> SEQUENCE: 3
gcacagattc tgagtaacca taat                                                24

<210> SEQ ID NO 4
<211> LENGTH: 23
<212> TYPE: DNA
<213> ORGANISM: Artificial Sequence
<220> FEATURE:
<223> OTHER INFORMATION: primer sequence

<400> SEQUENCE: 4
caactgtggt aaagcaatag tgt                                                 23

<210> SEQ ID NO 5
<211> LENGTH: 24
<212> TYPE: DNA
<213> ORGANISM: Artificial Sequence
<220> FEATURE:
<223> OTHER INFORMATION: primer sequence

<400> SEQUENCE: 5
taccaaatct ggatactata ccat                                                24

<210> SEQ ID NO 6
<211> LENGTH: 17
<212> TYPE: DNA
<213> ORGANISM: Artificial Sequence
<220> FEATURE:
<223> OTHER INFORMATION: primer sequence

<400> SEQUENCE: 6
atgtgggcga tcctatt                                                        17

<210> SEQ ID NO 7
<211> LENGTH: 17
<212> TYPE: DNA
<213> ORGANISM: Artificial Sequence
<220> FEATURE:
<223> OTHER INFORMATION: primer sequence

<400> SEQUENCE: 7
```

-continued ttgacaagcc caaagtt                                         17

<210> SEQ ID NO 8
<211> LENGTH: 21
<212> TYPE: DNA
<213> ORGANISM: Artificial Sequence
<220> FEATURE:
<223> OTHER INFORMATION: primer sequence

<400> SEQUENCE: 8
tgagtcgttt agagggcttc c                                    21

<210> SEQ ID NO 9
<211> LENGTH: 18
<212> TYPE: DNA
<213> ORGANISM: Artificial Sequence
<220> FEATURE:
<223> OTHER INFORMATION: primer sequence

<400> SEQUENCE: 9
aatctacggg ccacgcat                                        18

<210> SEQ ID NO 10
<211> LENGTH: 23
<212> TYPE: DNA
<213> ORGANISM: Artificial Sequence
<220> FEATURE:
<223> OTHER INFORMATION: primer sequence

<400> SEQUENCE: 10
tcctagggat taggccttca gta                                  23

<210> SEQ ID NO 11
<211> LENGTH: 22
<212> TYPE: DNA
<213> ORGANISM: Artificial Sequence
<220> FEATURE:
<223> OTHER INFORMATION: primer sequence

<400> SEQUENCE: 11
tgcattagca tgagagatcc tg                                   22

<210> SEQ ID NO 12
<211> LENGTH: 21
<212> TYPE: DNA
<213> ORGANISM: Artificial Sequence
<220> FEATURE:
<223> OTHER INFORMATION: primer sequence

<400> SEQUENCE: 12
tggttctaaa tgaggccgag g                                    21

<210> SEQ ID NO 13
<211> LENGTH: 19
<212> TYPE: DNA
<213> ORGANISM: Artificial Sequence
<220> FEATURE:
<223> OTHER INFORMATION: primer sequence

<400> SEQUENCE: 13
tcgctatgtg ggccagtct                                       19

<210> SEQ ID NO 14
<211> LENGTH: 22
<212> TYPE: DNA
<213> ORGANISM: Artificial Sequence

```
<220> FEATURE:
<223> OTHER INFORMATION: primer sequence

<400> SEQUENCE: 14
tttttgacaa tagccattcc ag                                              22

<210> SEQ ID NO 15
<211> LENGTH: 26
<212> TYPE: DNA
<213> ORGANISM: Artificial Sequence
<220> FEATURE:
<223> OTHER INFORMATION: primer sequence

<400> SEQUENCE: 15
accaacattt tcatactaag ataggg                                          26

<210> SEQ ID NO 16
<211> LENGTH: 23
<212> TYPE: DNA
<213> ORGANISM: Artificial Sequence
<220> FEATURE:
<223> OTHER INFORMATION: primer sequence

<400> SEQUENCE: 16
ttacaattga gaaacggctc ctg                                             23

<210> SEQ ID NO 17
<211> LENGTH: 22
<212> TYPE: DNA
<213> ORGANISM: Artificial Sequence
<220> FEATURE:
<223> OTHER INFORMATION: primer sequence

<400> SEQUENCE: 17
tggaggcatc acactacctg ac                                              22

<210> SEQ ID NO 18
<211> LENGTH: 23
<212> TYPE: DNA
<213> ORGANISM: Artificial Sequence
<220> FEATURE:
<223> OTHER INFORMATION: primer sequence

<400> SEQUENCE: 18
catctcccag gttcaagtga ttc                                             23

<210> SEQ ID NO 19
<211> LENGTH: 24
<212> TYPE: DNA
<213> ORGANISM: Artificial Sequence
<220> FEATURE:
<223> OTHER INFORMATION: primer sequence

<400> SEQUENCE: 19
ttcgcaccaa cattctccat tctg                                            24

<210> SEQ ID NO 20
<211> LENGTH: 22
<212> TYPE: DNA
<213> ORGANISM: Artificial Sequence
<220> FEATURE:
<223> OTHER INFORMATION: primer sequence

<400> SEQUENCE: 20
aatgcactca gaggactgga cc                                              22
```

```
<210> SEQ ID NO 21
<211> LENGTH: 24
<212> TYPE: DNA
<213> ORGANISM: Artificial Sequence
<220> FEATURE:
<223> OTHER INFORMATION: primer sequence

<400> SEQUENCE: 21
tggaacctat ctcctgttca tgtg                                              24

<210> SEQ ID NO 22
<211> LENGTH: 22
<212> TYPE: DNA
<213> ORGANISM: Artificial Sequence
<220> FEATURE:
<223> OTHER INFORMATION: primer sequence

<400> SEQUENCE: 22
ctcggactcc tgacatcaag tg                                                22

<210> SEQ ID NO 23
<211> LENGTH: 22
<212> TYPE: DNA
<213> ORGANISM: Artificial Sequence
<220> FEATURE:
<223> OTHER INFORMATION: primer sequence

<400> SEQUENCE: 23
gaaaccgtgc atctaacacc ag                                                22

<210> SEQ ID NO 24
<211> LENGTH: 22
<212> TYPE: DNA
<213> ORGANISM: Artificial Sequence
<220> FEATURE:
<223> OTHER INFORMATION: primer sequence

<400> SEQUENCE: 24
gctcagagtc atggtttcca gc                                                22

<210> SEQ ID NO 25
<211> LENGTH: 23
<212> TYPE: DNA
<213> ORGANISM: Artificial Sequence
<220> FEATURE:
<223> OTHER INFORMATION: primer sequence

<400> SEQUENCE: 25
gctgcataaa gtgtcacaga gcc                                               23
```

COMPARATIVE GENOMIC HYBRIDIZATION

FIELD OF THE INVENTION

The present invention relates to methods of comparative genomic hybridization and to nucleic acids attached to a solid substrate suitable for comparative genomic hybridization.

BACKGROUND OF THE INVENTION

Chromosome abnormalities are often associated with genetic disorders, degenerative diseases, and cancer. Chromosomal abnormalities can be of several types, including extra or missing individual chromosomes, extra or missing portions of a chromosome, breaks and chromosomal rearrangements Chromosomal rearrangements include translocations (transfer of a piece from one chromosome onto another chromosome), dicentrics (chromosomes with two centromeres), inversions (reversal in polarity of a chromosomal segment), insertions, amplifications, and deletions.

The detection of chromosomal abnormalities in cells is important for many reasons, not the least being the detection of chromosomal abnormalities for prenatal and pre-implantation genetic diagnosis, and the determination of the karyotype of some cancers.

Prenatal diagnosis involves the genetic testing of foetal material. Typically, this involves removal of amniotic fluid surrounding the foetus and the analysis of cells in the fluid for chromosomal abnormalities. Prenatal diagnosis is important for the detection of foetuses that have significant chromosomal errors. Detectable chromosomal abnormalities occur with a frequency of approximately one in every 250 human births, and abnormalities that involve deletions or additions of chromosomal material often lead to foetal death or to serious mental and physical defects. For example, Down Syndrome can be caused by having three copies of chromosome 21 instead of the normal two copies, or by a segmental duplication of a subregion on chromosome 21.

Pre-implantation genetic diagnosis (PGD) involves the testing of genetic material from an embryo or an egg (oocyte) prior to implantation. Typically, this process involves the removal and analysis of one or more cells from an embryo fertilized in vitro, in order to determine if the embryo is suitable for implantation. In the case of maternally derived chromosomal abnormalities, the polar body from an oocyte can also be removed and the presence of a chromosomal abnormality detected.

Pre-implantation genetic diagnosis for chromosomal abnormalities is important for detecting embryos or oocytes that are suitable for implantation. Early human embryos have a very high frequency of chromosomal errors including aneuploidy, polyploidy and mosaicism, and it is likely that these chromosomal errors are responsible for the significant rate of implantation failure of in vitro fertilized embryos. In addition, where there is a possibility that an embryo or oocyte may contain a known chromosomal abnormality inherited from one of the parents, pre-implantation diagnosis can also be performed to select embryos or oocytes that do not have the known chromosomal abnormality.

The deletion or multiplication of copies of whole chromosomes or chromosomal segments also often occurs in cancerous cells and in many cases these chromosomal abnormalities contribute to the cells acquiring a cancerous phenotype. The detection of such chromosomal abnormalities is not only important for understanding the genetic basis of how some cells progress from a non-cancerous state to a cancerous state, but in some cases may provide useful information as to the diagnosis and treatment of a specific cancer.

Traditionally, cytogenetic or fluorescence in situ hybridization (FISH) techniques have been used for detecting chromosomal abnormalities. However, comparative genomic hybridization (CGH) now provides a powerful method to overcome many of the limitations of the traditional cytogenetic and FISH approaches. CGH involves the comparative, multi-colour hybridization of a reference nucleic acid population labelled in one fluorescent colour and a sample nucleic acid population labelled in a second fluorescent colour to all or part of a reference genome, such as a human metaphase chromosome spread. Comparison of the resulting fluorescence intensity at locations in the reference genome permits determination of the copy number of chromosomal sequences in the sample population.

Although CGH has provided an improvement over traditional cytogenetic and FISH technologies, there are still many deficiencies associated with CGH, including the length of time required to perform the analysis. For example, standard CGH with metaphase spreads takes at least 72 hours to complete, and if PGD is being performed on a single cell taken from an embryo, then embryo cryopreservation before implantation must be performed so as to allow sufficient time to complete the procedure.

The present invention relates to the identification of an improved method for performing comparative genomic hybridization and to nucleic acid arrays suitable for comparative genomic hybridization.

Throughout this specification reference may be made to documents for the purpose of describing various aspects of the invention. However, no admission is made that any reference cited in this specification constitutes prior art in particular, it will be understood that the reference to any document herein does not constitute an admission that any of these documents forms part of the common general knowledge in the art in Australia or in any other country. The discussion of the references states what their authors assert, and the applicant reserves the right to challenge the accuracy and pertinency of any of the documents cited herein.

SUMMARY OF THE INVENTION

The present invention provides a method of comparing at least one chromosome or part thereof from a cell with a first karyotype with the corresponding chromosome or part thereof from a cell with a second karyotype, the method including the steps of:
 (a) amplifying DNA from an isolated chromosome or part of an isolated chromosome;
 (b) attaching the amplified DNA to a solid substrate;
 (c) amplifying DNA from one or more cells with a first karyotype and amplifying DNA from one or more cells with a second karyotype;
 (d) labelling the amplified DNA from the one or more cells with a first karyotype with a first label, and labelling the amplified DNA from the one or more cells with a second karyotype with a second label, wherein the first and second labels are detectably different;
 (e) hybridizing the amplified and labelled DNA from the one or more cells with a karyotype to the amplified DNA attached to the solid substrate, and hybridizing the amplified and labelled DNA from the one or more cells with a second karyotype to the amplified DNA attached to the solid substrate; and (f) comparing the relative amount of first and second labels hybridized to the amplified DNA attached to the solid substrate.

The present invention also provides a method of detecting a chromosomal abnormality in a cell with an unknown karyotype, the method including the steps of:

(a) amplifying DNA from an isolated chromosome or part of an isolated chromosome;

(b) attaching the amplified DNA to a solid substrate;

(c) amplifying DNA from one or more cells with an unknown karyotype and amplifying DNA from one or more cells with a reference karyotype;

(d) labelling the amplified DNA from the one or more cells with an unknown karyotype with a first label, and labelling the amplified DNA from the one or more cells with a reference karyotype with a second label, wherein the first and second labels are detectably different;

(e) hybridizing the amplified and labelled DNA from the one or more cells with an unknown karyotype to the amplified DNA attached to the solid substrate, and hybridizing the amplified and labelled DNA from the one or more cells with a reference karyotype to the amplified DNA attached to the solid substrate; and (f) detecting the presence of a chromosomal abnormality in the cell with the unknown karyotype by comparing the relative amount of the first label hybridised to the amplified DNA attached to the solid substrate to the amount of second label hybridised to the amplified DNA attached to the solid substrate.

The present invention also provides a nucleic acid attached to a solid substrate, wherein the nucleic acid is derived from an isolated chromosome or part of an isolated chromosome and the nucleic acid is depleted of repetitive sequences.

The present invention also provides an array of nucleic acids attached to a solid substrate, wherein each nucleic acid in the array is derived from an isolated chromosome or part of an isolated chromosome and each nucleic acid is depleted of repetitive sequences.

The present invention also provides a nucleic acid attached to a solid substrate, wherein the nucleic acid is derived from randomly primed amplification of an isolated chromosome or part of an isolated chromosome and the nucleic acid is depleted of one or more of repetitive sequences, non-chromosomal sequences or sequences that are over-represented due to amplification.

The present invention further provides an array of nucleic acids attached to a solid substrate, wherein each nucleic acid in the array is derived from randomly primed amplification of an isolated chromosome or part of an isolated chromosome and each nucleic acid is depleted of one or more of repetitive sequences, non-chromosomal sequences or sequences that are over-represented due to amplification of the chromosome or part thereof.

The present invention also provides a nucleic acid derived from randomly primed amplification of an isolated chromosome or part of an isolated chromosome, wherein the nucleic acid is depleted of repetitive sequences.

The present invention arises out of studies into the detection of trisomies 13 and 18 in single cells of amniocytes and lymphocytes. In particular, it has been surprisingly found that the detection of such trisomies in a single cell by comparative genomic hybridization may be markedly improved by replacing the metaphase spreads normally employed with the products of randomly primed amplification of an isolated chromosome or part thereof attached to a solid substrate. Comparative genomic hybridization performed in this way requires less time (approximately 30 hours in total) to perform than traditional methods using metaphase spreads.

Various terms that will be used throughout the specification have meanings that will be well understood by a skilled addressee. However, for ease of reference, some of these terms will now be defined.

The term "cell" as used throughout the specification is to be understood to mean a somatic cell, a germ cell, a cell of any ploidy, or any cell derived body having one or more chromosomes (or a part of one or more chromosomes) therein. Examples of cell derived bodies include the polar body associated with an unfertilised oocyte, a polar body extruded by an oocyte at the time of oocyte fertilization by a sperm, a nucleus isolated from a cell or part of a nucleus, a mitochondria, or a chloroplast.

The term "karyotype" as used throughout the specification is to be understood to mean the chromosomal constitution of a cell, which may vary between individuals of a single species.

In this regard, the term "unknown karyotype" is to be understood to mean that the karyotype of one or more chromosomes in a cell is not known. The term "reference karyotype" is to be understood to mean the karyotype of a cell that is used as the karyotype against which the karyotype of another cell is tested. The cell with the reference karyotype may have a known karyotype, such as a normal karyotype or a known deletion or multiplication of a specific chromosome, or alternatively, may have an unknown karyotype of one or more chromosomes. Typically, the cell with an unknown karyotype will be a cell from a foetus, an embryo, an oocyte or a cancer cell, and the cell with the reference karyotype will be the same type of cell or a similar cell with a normal karyotype.

The term "isolated chromosome or part of an isolated chromosomes" as used throughout the specification is to be understood to mean an isolated chromosome or any part of an isolated chromosome. In this regard, it is to be understood that part of a chromosome will include a part of a chromosome, isolated for example by microdissection or by flow cytometry, or any clone containing chromosomal (genomic) DNA. Examples of such clones include BAC, YAC and P1 clones containing genomic DNA, or any other clone having genomic DNA cloned into a suitable vector.

In this regard, it is also to be understood that the term "chromosome" means any chromosome present in a cell of any ploidy (haploid, diploid or polyploid), including a sex chromosome, an autosome, a mitochondrial chromosome, a chloroplast chromosome, or an episome.

The term "amplifying" or variants thereof as used throughout the specification is to be understood to mean the production of additional copies of a nucleic acid sequence. For example, amplification may be achieved using polymerase chain reaction (PCR) technologies (essentially as described in Dieffenbach, C. W. and G. S. Dveksler (1995) PCR Primer, a Laboratory Manual, Cold Spring Harbor Press, Plainview, N.Y.) or by other methods of amplification, such as rolling circle amplification on circular templates, such as described in Fire, A. and Xu, S-Q. (1995) *Proc. Natl. Acad. Sci* 92:4641-4645.

In this regard, the term "randomly primed amplification" will be understood to mean amplification utilising one or more primers that results in amplification of substantially the entire target. For example, random amplification may be achieved with the use of one or more primers including a sequence of one or more random nucleotides, the sequence of random nucleotides being sufficiently long so as to enable the primer to hybridize to the target nucleic acid under selected conditions at random positions and serve as a primer for extension by a polymerase. For example, the primer may be a primer including a stretch of six or more contiguous nucleotides of random sequence.

Alternatively, random amplification may be achieved with one or more primers of fixed sequence, but with the stringency of the amplification reaction sufficiently low to enable random amplification of the target, particularly in the early cycles of the amplification process.

In addition, it will be appreciated that amplification of DNA from one or more cells not only includes the amplification of the entire chromosomal content of one or more cells, but also includes the amplification of an isolated chromosome, or any part thereof, derived from one or more cells. For example, the DNA amplified for analysis could be a single chromosome isolated by microdissection or flow cytometry, a part of a chromosome isolated by microdissection, or part of a chromosome being a cloned fragment of genomic DNA.

The term "attaching" or variants thereof as used throughout the specification in relation to amplified DNA is to be understood to mean any form of immobilising amplified DNA to a solid substrate, including passive adsorption to the solid substrate, covalent linkage of the DNA to the solid substrate through appropriate chemical groups, or the use of specific chemical groups with high affinity for each other that allow the DNA to be immobilised on the solid substrate (eg biotin and streptavidin).

The term "solid substrate" as used throughout the specification is to be understood to mean any solid support that allows a nucleic acid to be spatially fixed to the support and which allows the nucleic acid to remain fixed to the support during hybridization. Examples of solid supports include glass, nylon or other type of membranes, filters, and chips.

In this regard, it will be understood that the nucleic acid need not be permanently fixed to the support, and that the nucleic acid may, if so desired, be fixed to the solid support so as to allow the removal of the nucleic acid from the support under selected conditions.

The term "chromosomal abnormality" as used throughout the specification is to be understood to mean any change or alteration in a part of a chromosome that may be detected by hybridisation using comparative genomic hybridization.

The term "germ cell" as used throughout the specification is to be understood to mean a reproductive cell, a gamete, or a cell that will develop into a reproductive cell. For example, a germ cell includes a spermatocyte or an oocyte.

The term "repetitive sequences" as used throughout the specification is to be understood to mean any sequence present in a nucleic acid that is present in more than one copy in the genome. Each copy of a repetitive sequence need not be identical to all the others, as long as the sequences are sufficiently similar that under the hybridization conditions being used the same fragment of probe nucleic acid is capable of forming stable hybrids with each copy. Examples of repetitive sequences include simple repeated DNA (eg Alu or Kpn elements), satellite repeats, mini-satellite repeats, chromosome-specific repeats, micro-satellite repeats, repeated genes (eg rRNA genes), sequences derived from transposable elements (eg transposons with DNA or RNA intermediates), elements derived from multiple copies of viruses such as retroviruses, repeats associated with centromeres or telomeres, or repeats associated with heterochromatin.

The term "nucleic acid" as used throughout the specification is to be understood to mean a polynucleotide, being composed of deoxyribonucleotides or ribonucleotides in either single-stranded or double-stranded form.

The term "isolated" as used throughout the specification in relation to a nucleic acid is to be understood to mean a nucleic acid separated from at least one other component (e.g., nucleic acid or polypeptide) present with the nucleic acid in its natural source.

The term "non-chromosomal sequences" as used throughout the specification is to be understood to mean any sequence in a nucleic acid sample that is not normally present in the nucleotide sequence of the genome of the nucleic acid sample, or the nucleotide sequence of one or more chromosomes or part thereof. Examples of such non-chromosomal sequences include sequences derived from a vector or plasmid, or contaminating sequences that may be present in a nucleic acid sample due to its preparation, such as bacterial sequences (eg *E.coli*).

The phrase "sequences that are over-represented due to amplification" or the term "over-represented sequences" as used throughout the specification is to be understood to mean those sequences present after amplification of the target that have been disproportionately amplified in comparison to other sequences normally present in the target.

BRIEF DESCRIPTION OF THE FIGURES

FIG. 10 in the bottom panel shows the results of an array CGH experiment of 100 fibroblast cells (47, XY, +18, Cy3) versus a pooled mixture (46, XY, Cy5) of 5 up to 10 single normal male cells.

FIG. 13 bottom panel shows agarose electrophoresis of DOP-PCR-amplified repeat-depleted BAC's DNA. The origins of samples are indicated above each lane: 1 (RP-11-265k23), and 2 (a mixture of RP-11-354m20m, RP-11-280F22, RP-11-113m14, RP-11-70E19, RP-11-10P15, and RP-11-506P9). DNA markers were SPP-1/EcoRI ($M_1$) and pUC19/HpaII ($M_2$).

FIG. 14 bottom panel shows agarose electrophoresis of DOP-PCR products using Expanded Long Template PCR-amplified products as templates. The origins of DYS loci are indicated above each lane. DNA markers were SPP-1/EcoRI ($M_1$) and pUC19/HpaII ($M_2$).

FIG. 15 in the top panel shows agarose gel electrophoresis of Cy3labelled female single-cell SEP-PCR products. PCR amplification was conducted using four different conditions and four single cells were separately amplified under each of these conditions. The origin of each sample is indicated above each lane. DNA markers were SPP-1/EcoRI ($M_1$) and pUC19/HpaII ($M_2$). Note that each labelled product gives a smear on a 1% Agarose gel ranging from 300 bp to 2,500 bp and containing two specific bands approximately at 450 bp and 600 bp. FIG. 15 in the bottom panel shows agarose gel electrophoresis of Cy5-labelled male single-cell SEP-PCR products. PCR amplification was conducted using four different conditions (details see context above) and four single cells were separately amplified under each of these conditions. The origin of each sample is indicated above each lane. DNA markers were SPP-1/EcoRI ($M_1$) and pUC19/HpaII ($M_2$). Note that each labelled product gives a smear on a 1% Agarose gel ranging from 300 bp to 2,500 bp.

GENERAL DESCRIPTION OF THE INVENTION

Figure 1:
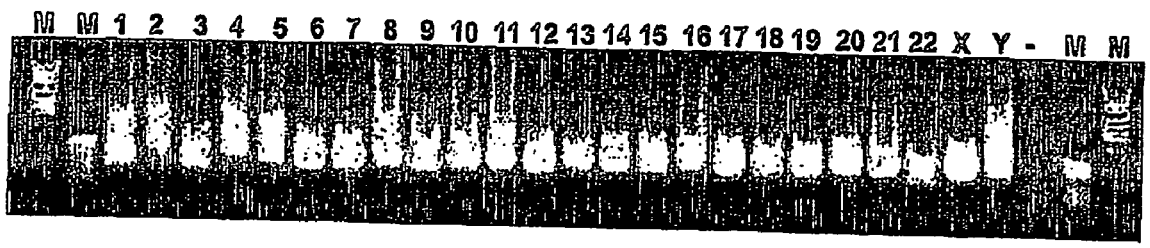
FIG. 1 shows electrophoresis of re-amplified DNA libraries of human chromosomes (autosomes 1-22; sex chromosomes X, Y) as described in Example 2. Size markers (λ HindIII, Puc19 HpaII) are also shown.

As mentioned above, in one form the present invention provides a method of comparing at least one chromosome or part thereof from a cell with a first karyotype with the corresponding chromosome or part thereof from a cell with a second karyotype, the method including the steps of:
(a) amplifying DNA from an isolated chromosome or part of an isolated chromosome;
(b) attaching the amplified DNA to a solid substrate;
(c) amplifying DNA from one or more cells with a first karyotype and amplifying DNA from one or more cells with a second karyotype;
(d) labelling the amplified DNA from the one or more cells with a first karyotype with a first label, and labelling the amplified DNA from the one or more cells with a second karyotype with a second label, wherein the first and second labels are detectably different;
(e) hybridizing the amplified and labelled DNA from the one or more cells with a first karyotype to the amplified DNA attached to the solid substrate, and hybridizing the amplified and labelled DNA from the one or more cells with a second karyotype to the amplified DNA attached to the solid substrate; and
(f) comparing the relative amount of first and second labels hybridized to the amplified DNA attached to the solid substrate.

This form of the present invention allows the number of copies of one or more chromosomes, or a region of one or more chromosomes, in a cell with a first karyotype to be compared to a corresponding chromosome or region in a cell with a second karyotype. As such, this form of the present invention may be used, for example, in prenatal genetic diagnosis, pre-implantation genetic diagnosis, gender determination or selection, or the determination of the karyotype of cancerous or other somatic cells.

Preferably, the method of this form of the present invention is used for pre-implantation diagnosis of an embryo or an oocyte, or for the prenatal diagnosis of a foetus for a chromosomal abnormality.

Preferably, the cell with the first karyotype is of unknown karyotype, and the cell with the second karyotype is of known karyotype. For example, the cell with the first karyotype may have an unknown chromosomal abnormality at a particular chromosomal location, and the cell with the second karyotype may have a known normal chromosome at the corresponding chromosomal location.

In this regard, this form of the present invention is useful for the detection of gross chromosomal differences in a cell, such as deletions, duplications or amplifications. Examples of conditions that may be amenable to detection by the present invention include Trisomy 21, 13 and 18 and the detection of missing chromosomes, such as occurs in Turner's syndrome (46, XO).

It will be appreciated that the present invention may be used to compare all chromosomes in a cell with a first karyotype with a cell with a second karyotype. However, depending on the amplified DNA being attached to the solid substrate, the invention may also be used for comparing parts of one or more specific chromosomes between cells.

The chromosome to be compared may be any chromosome present in a cell of any ploidy (haploid, diploid or polyploid), including a sex chromosome, an autosome, a mitochondrial chromosome, a chloroplast chromosome or an episome. Preferably, the chromosome is a sex chromosome or an autosome. Most preferably, the chromosome is an autosome.

Similarly, the part of the isolated chromosome to be compared may be part of any chromosome present in a cell of any ploidy (haploid, diploid or polyploid) including a sex chromosome, an autosome, a mitochondrial chromosome, a chloroplast chromosome or an episome. Preferably, the part of the chromosome is part of a sex chromosome or an autosome. Most preferably, the part of the chromosome is part of an autosome.

The cell with the first karyotype may be any cell for which the karyotype (first karyotype) is to be compared to the karyotype (second karyotype) of another cell. The cell with the first karyotype may be a eukaryotic or a prokaryotic cell. Preferably, the cell is a eukaryotic cell. More preferably, the cell is an animal or human cell. Most preferably, the cell is a human cell.

Preferably, the cell with the first karyotype is a foetal cell, a cell derived from an embryo, a germ cell, a cancerous cell or any other type of somatic cell with a karyotype to be compared to the karyotype of another cell. More preferably the cell with the first karyotype is a foetal cell, an embryonic cell (including a blastomere) or a germ cell. Most preferably, the cell is an embryonic cell or an oocyte.

Examples of a foetal cell include a foetal cell taken from the amniotic fluid surrounding the foetus, a foetal blood cell taken from the maternal circulation, or a foetal cell taken from the mothers reproductive tract (eg cervical or vaginal lavage). In this regard, foetal blood cells, unlike mature blood cells, are nucleated and can be isolated from the maternal circulation.

In the case of an embryonic cell, a small number of cells (usually one or two cells) may be removed from an embryo. In this procedure, one or more cells in an embryo may be removed by cleavage stage embryo biopsy. This procedure is usually performed on day 3 of development, when the embryo is at the 6-8 cell stage. The biopsy consists of two stages. The first is to make a hole in the zona pellucida that surrounds the embryo at this time, usually using acid Tyrodes solution or a non-contact laser. Once the hole is made, the cell may then be removed from the embryo.

In the case of a germ cell, for example an oocyte or sperm cell, the germ cell may be analysed directly. Alternatively, in the case of screening for maternal abnormalities, a polar body from the oocyte may be isolated.

In the case of a cancerous cell or any other somatic cell, one or more cells may be obtained from a subject by a suitable method known in the art, such as direct biopsy of cells or isolation from blood.

In this regard, a large number of cells may not necessarily be associated with a more accurate determination of karyotype, and in some cases it may be preferable that a relatively small number of cells (eg 1 to 20 cells) is isolated.

The cell with the second karyotype may be any cell for which the karyotype of the cell with the first karyotype is to be compared. Preferably, the cell with the second karyotype is of the same type or a similar type as the cell with the first karyotype.

The isolated chromosome in the various forms of the present invention may be any chromosome that has been substantially purified from other chromosomes by a method known in the art. For example, the chromosome may be isolated by microdissection as described in Meltzer et al. (1992) *Nature Genetics* 1:24-28. Alternatively, the chromosome may be isolated by flow cytometry as described in Telenius et at. (1992) *Genes, Chromosomes & Cancer* 4:257-263.

In the case of microdissection, cells are first treated to force them into metaphase and an entire chromosome may be isolated with the use of a very fine needle. In the case of flow cytometry, chromosomes may be stained with specific chromosomal staining reagents and the chromosomes isolated by the extent of fluorescence associated with each of the chromosomes via sorting.

A part of an isolated chromosome in the various forms of the present invention may be any part of an isolated chromosome for which the karyotype is to be compared with the corresponding part of the same chromosome in another cell.

A part of a chromosome may be isolated by a suitable method known in the art including the microdissection of specific chromosomal bands from metaphase chromosomes as discussed above.

Alternatively, a part of a chromosome may be a cloned fragment of a chromosome, isolated by cloning a fragment of genomic DNA into a suitable vector. Methods for the isolation of large and small genomic fragments and their cloning into vectors are essentially as described in Sambrook, J. Fritsch, E. F. and Maniatis, T. Molecular Cloning: A Laboratory Manual 2nd. ed. Cold Spring Harbor Laboratory Press, New York. (1989). For example, to produce large genomic fragments for cloning into a vector such as a YAC, partial digestion of genomic DNA with a restriction endonuclease may be performed and the resulting fragments cloned into the vector. The isolated vector with cloned insert DNA may then be purified by a suitable method known in the art. Examples of suitable vectors for cloning large genomic fragments are YAC vectors, BAC vectors, P1 vectors or cosmids.

Amplification of the DNA from an isolated chromosome or part of an isolated chromosome in the various forms of the present invention may be achieved by a suitable method known in the art that allows the production of additional copies of the DNA. For example, in the case of an entire chromosome isolated by microdissection or flow cytometry, or a part thereof isolated by microdissection, the DNA may be amplified using PCR technology, essentially as described in Dieffenbach, C. W. and G. S. Dveksler (1995) PCR Primer, a Laboratory Manual, Cold Spring Harbor Press, Plainview, N.Y.

In this regard, a nucleic acid will be derived from an amplification product if the nucleic acid has been produced by an amplification process, and includes a nucleic acid derived from an amplification process that has subsequently been subjected to one or more treatments after amplification.

In the case of part of a chromosome cloned into a circular vector, amplification may be achieved for example by PCR amplification or by the use of rolling circle amplification as described in Fire, A, and Xu, S-Q. (1995) *Proc. Natl. Acad. Sci* 92:4641-4645.

Preferably the amplification of the DNA from an isolated chromosome or part of an isolated chromosome will result in the amplification of substantially the entire target.

Accordingly, it is preferred that the amplification of the isolated chromosome or a part of an isolated chromosome in the various forms of the present invention is randomly primed amplification to achieve amplification of substantially the entire target.

Amplification of the DNA from an isolated chromosome or part there of will be performed with one or more appropriate primers. As discussed above, preferably the one or more primers used will result in the random amplification of the isolated chromosome or part of the isolated chromosome.

Preferably, the one or more primers used is an oligonucleotide including one or more nucleotides of random sequence. More preferably, the one or more primers is an oligonucleotide including one or more contiguous nucleotides of random sequence. More preferably, the one or more of primers is an oligonucleotide that includes six or more contiguous nucleotides of random sequence, such as a DOP primer (degenerate oligonucleotide primer). Most preferably, the one or more primers is a primer with the following nucleotide sequence:

5'-CCGACTCGAGNNNNNNATGTGG-3';  (SEQ ID NO. 1)

where NNNNNN represents the degenerate sequence. "N" is any nucleotide ie N represents the four possible nucleotides in the DNA sequence: "A", "T", "C" and "G" for Adenine, Thymine, Cytosine and Guanine, respectively. As such, the degenerate sequence contain mixtures of various nucleotide sequences including all possible combinations of A, T, C and G at the "N" positions.

If so desired, the nucleotide sequence of the degenerate sequence can also be biased towards a particular nucleotide composition, for example GC or AT richness.

In the case of amplification using DOP primers on an isolated chromosome, or a part of a chromosome isolated by microdissection or by cloning into a vector; the amplification may be performed essentially as described in Telenius et al. (1992) Genomics 18:718-725 (1992). Briefly, the amplification is performed under low stringency conditions for a low number of cycles (eg five cycles) and a second stage amplification performed under more stringent conditions for a larger number of cycles (eg 35 cycles).

Alternatively, random primed amplification may be achieved using one or more primers of fixed sequence and performing a low number of cycles of amplification under low stringency conditions that allow the one or more primers to prime synthesis randomly throughout the target, followed by a second stage amplification performed under more stringent conditions for generally a larger number of cycles.

In addition, to account for regions of small chromosomes that may present a difficulty in achieving randomly primed amplification of substantially the entire target, region specific primers can also be used in conjunction with other primers that allow random amplification. For example, primers to specific regions of chromosomes 21 and 22 may be used in conjunctions with DOP primers.

Accordingly, in a preferred form of the present invention the amplification of DNA from the isolated chromosome or part of the isolated chromosome further includes amplification of a specific chromosomal region.

Other suitable techniques for amplification of the isolated chromosome or part of an isolated chromosome include primer-extension pre-amplification PCR (PEP-PCR) which may be performed essentially as described in Zhang et al. (1992) Proc Natl. Acad. Sci 89:5847-5851); ligation mediated PCR, which may be performed essentially as described in Klein et al. (1999) Proc. Natl. Acad. Sci. 96:4494-4499); or alu-PCR, which may be performed essentially as in Nelson et al. (1989) Proc. Natl. Acad. Sci. 86:6686-6690).

In the case of using rolling circle amplification on a cloned genomic insert in a circular vector, rolling circle amplification may be performed using suitable conditions known in the art, for example as described in Fire, A. and Xu, S-Q. (1995) Proc. Natl. Aced. Sci 92:4641-4645.

Preferably, the amplified DNA from the isolated chromosome or part of an isolated chromosome in the various forms of the present invention is further subjected to size selection before attachment to the solid substrate. Preferably, the amplified DNA attached to the solid substrate is less than 10 kb in size. More preferably, the amplified DNA attached to the solid substrate is less than 3 kb in size.

Size selection may be performed by a suitable method known in the art. For example, the amplified DNA may be electrophoresed on an agarose gel, and DNAs with a size in the range from 150 to 3000 bp may be isolated.

In a preferred form of the present invention, the nucleic acid attached to the solid substrate is the product of randomly primed amplification of an isolated chromosome or part of an isolated chromosome, wherein the nucleic acid has been size selected.

In this case, the randomly amplified DNA attached to the solid substrate is preferably less than 10 kb in size. More preferably, the randomly amplified DNA attached to the solid substrate is less than 3 kb in size. For example, the randomly amplified DNA may be electrophoresed on an agarose gel, and DNAs with a size in the range from 150 to 3000 bp may be isolated.

In a further preferred embodiment, the amplified DNA from the isolated chromosome or part of an isolated chromosome in the various forms of the present invention is depleted of one or more of repetitive sequences, non-chromosomal sequences, or sequences that are over-represented due to amplification. A number of methods known in the art can be used to deplete the amplified DNA of such sequences.

Repetitive sequences are sequences present in more than one copy in the target sequence to be amplified. Non-chromosomal sequences are sequences that are not normally present in the nucleotide sequence of a chromosome or part thereof, such as sequences derived from a vector or plasmid, or contaminating sequences that may be present in the originally target sample to be amplified, such as bacterial sequences (eg sequences derived from E.coli). Sequences that are over-represented due to amplification of the chromosome are those sequences present after amplification of the target that have been disproportionately amplified in comparison to other sequences normally present in the target.

Repetitive sequences and/or non-chromosomal sequences may be removed either prior to amplification or after amplification. For example, chromosomal DNA may be isolated and repetitive sequences and/or non-chromosomal sequences removed. Alternatively, the DNA may first be amplified with appropriate primers and the repetitive DNA sequences and/or non-chromosomal sequences removed from the amplified pool of nucleic acids.

Examples of repetitive sequences include simple repeated DNA (eg Alu or Kpn elements), satellite repeats, mini-satellite repeats, chromosome-specific repeats, micro-satellite repeats, repeated genes (eg rRNA genes), sequences derived from transposable elements (eg transposons with DNA or RNA intermediates), elements derived from multiple copies of viruses such as retroviruses, repeats associated with centromeres or telomeres, or repeats associated with heterochromatin.

A number of methods known in the art can be used to. remove repetitive sequences. For example, in many genomes, such as the human genome, a major portion of repetitive DNA is contained in a few families of highly repeated sequences such as Alu. To remove such repetitive sequences, a blocking procedure can be used. These methods primarily exploit the fact that the hybridization rate of complementary nucleic acid strands increases as their concentration increases. Thus, if a mixture of nucleic acid fragments is denatured and incubated under conditions that permit hybridization, the sequences present at high concentration will become double-stranded more rapidly than the others. The double-stranded nucleic add can then be removed by the direct removal of these sequences by a method known in the art.

For example, single- and double-stranded nucleic acids have different binding characteristics to hydroxyapatite. Such characteristics provide a basis commonly used for fractionating nucleic acids. The fraction of genomic DNA containing sequences with a particular degree of repetition can be obtained by denaturing genomic DNA, allowing it to reassociate under appropriate conditions, followed by separation using hydroxyapatite. Such techniques are as described in Britten et al., "Analysis of Repeating DNA Sequences by Reassociation" Methods In Enzymology 22:363-418 (1974).

Examples of such sequences that can be used to deplete the amplified DNA of repetitive sequences include human Cot-1 DNA and Alu—repeat containing DNAs.

Alternatively, reaction with immobilized nucleic acid may be performed. For example, minimally sheared human genomic DNA is bound to diazonium cellulose or a like support. The amplified DNA, appropriately cut into fragments, is hybridized against the immobilized DNA to Cot values in the range of about 1 to 100. The material that does not bind to the immobilised nucleic acid may then be attached to the solid substrate.

In the case of repetitive sequences depleted from a genomic clone, the repetitive sequences may also be depleted from a clone of genomic DNA (eg removed during the cloning process) and the resulting clone depleted of repetitive sequences used for amplification. Alternatively, the repetitive sequences may be depleted as above after amplification of the clone.

Similarly, non-chromosomal sequences may be depleted before or after amplification of the target sequence. In a similar manner to as described above for the depletion of repetitive sequences, non-chromosomal sequences may be depleted by using non-chromosomal sequences in excess in a hybridization reaction with the target or the amplified DNA, or by attaching the non-chromosomal sequences to a solid support and using these sequences to deplete the DNA of these sequences.

In the case of depleting over-represented sequences due to amplification, these sequences may be depleted from the target by similar methods described above, or the over-represented sequences may be depleted after amplification. As will be appreciated, an understanding of the actual sequence being over-represented is necessary, and will depend on the primers being used and the nature of the target being amplified.

Over represented sequences and repetitive sequences may be depleted together by amplifying a source of repetitive sequences with the same primers used to amplify the DNA from an isolated chromosome or part of an isolated chromosome. The amplified repetitive nucleic acid can then be used to deplete the amplified DNA of over represented and repetitive sequences. For example, DOP-PCR may be performed on Cot-1 DNA, and the resultant amplification products used to deplete the amplified DNA from an isolated chromosome or part of an isolated chromosome.

The solid substrate in the various forms of the present invention is any solid support that allows a nucleic acid to be spatially fixed to the support and which allows the nucleic acid to remain fixed to the support during and after hybridization. Examples of solid supports include glass, nylon or other type of membranes, filters, and chips.

The amplified DNA may be attached to a solid substrate in the various forms of the present invention by a suitable method known in the art, including passive adsorption or covalent linkage. For example, the amplified DNA may be attached to a glass substrate by passive adsorption by spotting samples onto a Polysine™ microscope glass slide (Menzel-Glaser, Germany) and processing of the slide by dehydration, snap-drying, fixation through UV cross linking, and chemical blocking by using succinic anhydride. In the case of covalent linkage, the amplified DNA may be attached to the solid substrate by a suitable method known in the art.

It is preferred that more than one amplified DNA is attached to the solid substrate, to produce an array of deposited DNAs. Such an array can be manufactured in any desired manner known in the art, including robotic deposition of the amplified DNAs. Examples of methods for producing arrays are essentially as described in U.S. Pat. Nos. 5,486,452, 5,830,645, 5,807,552, 5,800,992 and 5,445,934.

Any suitable amount of DNA may be deposited on the solid substrate. The amount of nucleic acid deposited can be from about 0.05 nl to about 5.0 nl of a nucleic acid solution of 0.15-1 µg/µl nucleic acid concentration. For example, for a density of 1,000 DNAs deposited/cm, the individual amount deposited is about 0.2 nl to about 2.0 nl of 1 µg/µl solution. The DNA is provided in any solvent that will permit deposition of the nucleic acid.

The array having deposited DNAs may be produced in any arrangement. For example, the DNAs can be located in one portion of the array or can be interspersed among other deposited nucleic acids. The regularity of a two dimensional array is preferred.

It is also preferred that the array include various control nucleic acids, such as, for example, spotted nucleic acids of known copy number for a particular expressed gene or genomic sequence. For example, genomic DNA extracted from cell lines with 1 or more copies of a particular chromosome can be used, or the entire DOP-PCR products of amplification of DNA from a single cell can also be used.

The number of cells to be analysed is not particularly limited, and may range from a single cell (for example isolated from an embryo) to a large number of cells (for example isolated from a tissue biopsy or blood). For example, the method of the present invention may be applied to PGD on a single cell isolated from an embryo or a polar body from an oocyte, prenatal diagnosis of foetal cells, or the determination of the karyotype of cancer cells or other somatic cells isolated from a subject by biopsy or isolated from the blood.

In the case of pre-natal diagnosis, for example, the number of cells to be analysed is also not particularly limited, and is preferably less than 500 cells, more preferably less than 400 cells and most preferably less than. 100 cells. A suitable range is 50-400 cells.

Preferably, the amplified DNA from one or more cells with a first karyotype is DNA amplified from 1 to 20 cells.

In a preferred form of the invention, the cell to be analysed is a single cell or a small number of cells, being in the range from 2 to 20 cells.

Preferably, the number of cells from which DNA is to be extracted and amplified is the same or similar between the cell or cells with the first karyotype and the cell or cells with the second karyotype. For example, in the case of PGD on a single cell from an embryo or the polar body from an oocyte, a single cell from another source will be preferably used for the comparison.

To obtain DNA from the cell for amplification in the various forms of the present invention, a suitable method known in the art for lysing the cell and obtaining the DNA may be used. For example, treatment of a cell with a hydroxide solution and subsequent neutralization lyses the cell and allows the extracted DNA to be directly amplified.

Preferably the amplification will result in the amplification of substantially the entire extracted DNA. Accordingly, it is preferred that the amplification of the DNA is randomly primed amplification.

Accordingly, the amplifying of DNA from one or more cells with a first karyotype and the amplifying of DNA from one or more cells with a second karyotype is preferably randomly primed amplification.

Amplification of the DNA from the cell in the various forms of the present invention will be performed with one or more appropriate primers. As discussed above, preferably the one or more primers used will result in the random amplification of the DNA.

To amplify DNA from one or more cells, the amplification of the extracted DNA may then be performed with one or more appropriate primers by a suitable method known in the art, such as PCR.

Preferably, the one or more of the primers used for amplification is an oligonucleotide including one or more nucleotides of random sequence. More preferably, the one or more primers is an oligonucleotide including one or more contiguous nucleotides of random sequence. More preferably, the one or more of the primers is an oligonucleotide that includes six or more contiguous nucleotides of random sequence, such as a DOP primer (degenerate oligonucleotide primer). Most preferably, the one or more primers is a primer with the following nucleotide sequence:

5'-CCGACTCGAGNNNNNNATGTGG-3'; (SEQ ID NO. 1)

where NNNNNN represents the degenerate sequence. "N" is any nucleotide ie N represents the four possible nucleotides in the DNA sequence: "A", "T", "C" and "G" for Adenine, Thymine, Cytosine and Guanine, respectively. As such, the degenerate probe sequences contain mixtures of various probes including all possible combinations of A, T, C and G at the "N" positions.

If so desired, the nucleotide sequence of the degenerate sequence can also be biased towards a particular nucleotide composition, for example GC or AT richness.

In the case of amplification using DOP primers, the amplification may be performed essentially as described in Telenius et al. (1992) *Genomics* 18:718-725 (1982). Briefly, the amplification is performed under low stringency conditions for a low number of cycles (eg five cycles) and a second stage amplification performed under more stringent conditions for a larger number of cycles (eg 35 cycles).

Alternatively, random primed amplification may be achieved using one or more primers of fixed sequence and performing a low number of cycles of amplification under low stringency conditions that allow the one or more primers to prime synthesis randomly throughout the target, followed by a second stage amplification performed under more stringent conditions for a larger number of cycles.

Other suitable techniques for amplification of the extracted DNA include primer-extension pre-amplification PCR (PEP-PCR) which may be performed essentially as described in Zhang et al. (1992) *Proc Natl. Acad. Sci* 89:5847-5851); ligation mediated PCR, which may be performed essentially as described in Klein et al. (1999) *Proc. Natl. Acad. Sci.* 96:4494-4499); or alu-PCR, which may be performed essentially as in Nelson et al. (1989) *Proc. Natl. Acad. Sci.* 86:6686-6690).

Amplification may be performed under suitable conditions known in the art. For example, for the amplification by PCR of genomic DNA isolated from a single lymphocyte cell isolated from blood, lysis of the single cell may be achieved by treatment with a lysis buffer (200 mM KOH, 50 mM dithiothreitol) for 10 min at 65° C. followed by neutralization with 300 mM KCl, 900 mM Tris-HCl, Ph 8.3, 200 mM HCl. To the lysed and neutralized solution may be added an appropriate PCR buffer, Taq polymerase and amplification performed using an initial denaturation step of 95° C. for 5 min and subsequent cycling conditions of 8 cycles of low stringent amplification of 94° C. for 1 min, 30° C. for 1.5 min, 72° C. for 3 min with a ramp of 1° C. per 4 seconds for increasing temperature from 30° C. to 72° C., followed by 26 cycles of high stringent amplification of 94° C. for 1 min, 62° C. for 1 min, 72° C. form 3 min with an addition of 14 seconds per cycle to the extension step. An extension step of 72° C. for 10 min may then be performed to complete the amplification.

Preferably, extracted DNA from the one or more cells with the first karyotype and extracted DNA from the one or more cells with the second karyotype are amplified with the same primers, and preferably also under the same conditions. In this way, the quality and quantity of the extension products resulting from the amplification reaction are comparable.

Preferably, the amplified DNA from one or more cells with a first karyotype and the amplified DNA from one or more cells with a second karyotype are both depleted of repetitive sequences. Methods for depleting the DNA amplified from cells is as described previously in relation to depletion of repetitive sequences from an isolated chromosome or part of an isolated chromosome.

Preferably the repetitive sequences are Cot-1 sequences.

It may also be desired to compare a specific chromosomal region or gene in the cell with a first karyotype with the same region or gene in the cell with a second karyotype.

Thus, a specific primer or the set of specific primers may be added to other primers that are present in the reaction mix. Alternatively, the specific primer or the set of specific primers may be used as the only primers to amplify the extracted DNA.

Examples of primers that may be used are primers that amplify a specific region of a chromosome, are primers to small chromosomes (eg chromosomes 21 and 22). In such a case, it may be preferable to add such primers to a set of primers that randomly amplify the genomic DNA, for example DOP primers.

In the situation where it is desired to amplify a specific chromosomal region, a specific locus, or one or more specific genes, primers to the particular region may be used alone or in combination with other primers, such as DOP primers to randomly amplify genomic DNA. For example, chromosomal regions including the regions involved in diseases such as thalassemia, Duchenne muscular dystrophy, X-linked disorders and Haemophilia may be amplified for analysis of chromosomal abnormalities. It will be appreciated in this regard that the method of the current invention is useful for the detection of major chromosomal abnormalities such as deletions and multiplications, and the specific loci being amplified will need to carry such abnormalities to allow their detection by the method of the present invention.

Suitable appropriate primers for amplification of specific chromosomal regions may be identified from the known nucleotide sequence. In the case of the amplification of specific chromosomal regions in humans, appropriate primers may be selected by consideration of the commercial Celera nucleotide sequence database or the publicly accessible nucleotide sequence database available from NCBI.

For example, exon 11 of the cystic fibrosis gene (CFTR) may be amplified using a nested PCR approach. For the first round, the following primers may be used:

5'-TGAAATAATGGAGATGCAATGTTC-3'; (SEQ ID NO. 2)
and

5'GCACAGATTCTGAGTAACCATAAT3' (SEQ ID NO. 3)

For the second round, the following primers may be used:

5'-CAACTGTGGTAAAGCAATAGTGT-3'; (SEQ ID NO. 4)
and

5'-TACCAAATCTGGATACTATACCAT-3' (SEQ ID NO. 5)

Suitable amplification conditions for the first round include 1/10th of the DOP-PCR mix from the amplification of the DNA from a single cell, 50 mM KCl, 10 mM Tris-HCl, pH 8.3, 100 µM each dNTP, 2.5 mM MgCl$_2$ and 1U Taq polymerase, using the following conditions in a MJ Researcher PTC-100 PCR machine with hot bonnet, place reaction tubes into 96° C. block and perform initial denaturation step of 94° C. for 5 min, cycling conditions of 94° C. for 30 sec, 62° C. for 45 sec, 72° C. for 45 sec, for 30 cycles. The second round PCR consists of 3 µl of the amplification products from the first round PCR, 50 mM KCl, 10 mM Tris-HCl, pH 8.3, 100 µM each dNTP, 2.5 mM MgCl$_2$ and 1U Taq polymerase. Cycling conditions use a MJ Researcher PTC-100 PCR machine with hot bonnet: and cycling conditions of 94° C. for 30 sec, 52° C. for 45 sec, 72° C. for 45 sec, for 30 cycles. After amplification, products can be sequenced essentially as described Hussey et al. (2002) *Mol. Hum. Reprod.* 8:1136-1143.

Labelling of amplified genomic DNA in the various forms of the present invention with a suitable label may be achieved by a suitable method known in the art. Labelling may occur after amplification, or alternatively, may occur during or as part of the initial amplification.

For example, direct labelling of the amplified genomic DNA described above may accomplished by further rounds of PCR incorporating a fluorescent moiety attached to a nucleotide to be incorporated. Other methods of indirect labelling are also known in the art. Alternatively, the amplified DNA may be labelled by subjecting the DNA to nick translation with a labelled nucleotide, essentially as described in Kirchhoff et al. (1998). *Cytometry* 31:163-173.

The amplified DNA from one or more cells with a first karyotype will be labelled with a first label, and the amplified DNA from one or more cells with a second karyotype will be a labelled with a second label that is detectably different from the first label. Examples of detectably different labels for incorporation into DNA include SpectrumGreen-dUTP and SpectrumRed-dUTP (both from Vysis), or Cy3-dUTP and Cy5-dUTP.

For hybridization of the amplified and labelled genomic DNAs to the DNA attached to the solid substrate in the various forms of the present invention, it is preferable that repetitive sequences, non-chromosomal sequences or sequences over-represented due to amplification, do not dominate the signal, and that they be depleted from the pool or that their ability to hybridize be suppressed as necessary.

Such sequences may be depleted either prior to amplification or after amplification. For example, genomic DNA may be extracted and repetitive sequences, non-chromosomal sequences or sequences over-represented due to amplification depleted. Alternatively, the genomic DNA may first be amplified with appropriate primers and then these sequences depleted from the amplified pool of nucleic acids.

A number of methods known in the art can be used to remove such sequences, and/or disable the hybridization capacity of such sequences.

For example, in many genomes, such as the human genome, a major portion of repetitive DNA is contained in a few families of highly repeated sequences such as Alu. To remove such repetitive sequences, a blocking procedure can be used. These methods primarily exploit the fact that the hybridization rate of complementary nucleic add strands increases as their concentration increases. Thus, if a mixture of nucleic acid fragments is denatured and incubated under conditions that permit hybridization, the sequences present at high concentration will become double-stranded more rapidly than the others. The double-stranded nucleic acid can then be removed and the remainder used in the hybridization, A blocking method is generally described in the context of Southern analysis by Sealy et al., "Removal of Repeat Sequences form Hybridization Probes", *Nucleic Acid Research* 13:1905 (1985).

Examples of such sequences that can be used to deplete the amplified DNA of repetitive sequences include human Cot-1 DNA and Alu—repeat containing DNAs.

Repetitive sequences may be depleted by the direct removal of these sequences by a method known in the art For example, single- and double-stranded nucleic acids have different binding characteristics to hydroxyapatite. Such characteristics provide a basis commonly used for fractionating nucleic acids. The fraction of genomic DNA containing sequences with a particular degree of repetition can be obtained by denaturing genomic DNA, allowing it to reassociate under appropriate conditions, followed by separation using hydroxyapatite. Such techniques are as described in Britten et al., "Analysis of Repeating DNA Sequences by Reassociation" *Methods in Enzymology* 22: 363-418 (1974).

Alternatively, the reaction with immobilized nucleic add may be performed. For example, minimally sheared human genomic DNA is bound to diazonium cellulose or a like support. The amplified genomic DNA, appropriately cut into fragments, is hybridized against the immobilized DNA to Cot values in the range of about 1 to 100.

Non-chromosomal sequences or over-represented sequences may be removed by similar methods as described above. Vector and/or contaminating sequences are used to deplete the DNA of the sequences in the case of non-chromosomal sequences, and over-represented sequences used to deplete the DNA in the latter case.

Over represented sequences and repetitive sequences may be depleted together by amplifying DNA from the one or more cells and using a source of repetitive sequences amplified with the same primers used to amplify the DNA from the one or more cells. The amplified repetitive nucleic acid can then be used in the hybridisation reaction. For example, DOP-PCR may be performed on Cot-1 DNA, and the resultant amplification products used to deplete the amplified DNA from the one or more cells if over represented sequences and repetitive sequences.

Hybridization of the amplified and labelled DNA to the amplified DNA attached to the solid substrate in the various forms of the present invention may be performed by a suitable method known in the art. The hybridization of the amplified DNA from the one or more cells with the first karyotype to the DNA attached to the solid substrate, and the hybridization of amplified DNA from the one or more cells with the second karyotype to the DNA attached to the solid substrate, may be performed concurrently or sequentially.

The DNA is hybridized to DNA attached to the solid substrate under appropriate conditions. The hybridization conditions include choice of buffer, denaturant, such as formamide, salt additives and accelerant. The buffer will preferably have a pH of about 6.8 to about 7.2, a salt content of about 1.5×SSC to about 2.5×SSC, and a formamide content of about 40-50%. Suitable conditions can include a temperature of about 40 to about 80 degrees centigrade for a time sufficient to detect signal over background for both genomic and expression of about 1 to about 72 hours, preferably 12-24 hours. Hybridization accelerators, such as dextran sulfate, can be used if desired. The post-hybridization wash is preferably at a stringency greater than that of the hybridization.

It is preferred that during hybridization an excess of unlabeled human repeat sequence DNA, such as Cot-1 DNA is also added. Use of unlabelled repeat sequence DNA in the hybridization mix is generally in amounts of about 0.01 to about 5.0 µg per ng of total labelled genomic DNA.

The hybridization can be performed in any suitable apparatus that will maintain the amplified and labelled DNA in contact with the DNA attached to the solid support, After hybridization, fluorescence intensity for each label is detected and determined by any suitable detector or reader apparatus and method. Laser-based array scanning detectors are known in the art The imaging apparatus and method in the various forms of the present invention may employ digital image processing algorithms used in a programmed computer for data analysis, storage and display of digital image data from the imaging apparatus. Any suitable digital image processing, data storage and display software can be used for analysis of the hybridization results.

The fluorescent data at each target element can be compared automatically to produce the ratio between the detectably different labels used.

The comparison of the relative amount of the first and second labels hybridised to the amplified DNA attached to the solid substrate may be used to detect whether the cell with the first karyotype has the same karyotype at a particular chromosomal position as the cell with the second karyotype, or alternatively, whether the cell with the first karyotype has a different karyotype at a particular chromosomal position as the cell with the second karyotype.

For the cell with the first karyotype to have the same karyotype as a cell with the second karyotype at a particular chromosomal location, preferably the ratio of the first (eg green) and second (eg red) labels hybridised to the amplified DNA will be in the range of 0.80 (ie ratio of red/green) for an autosome or 0.75 (ie ratio of red/green) for a sex chromosome to 1.20 (ie ratio of red/green) for an autosome or 1.25 (ie ratio of red/green) for a sex chromosome.

Alternatively, for the cell with the first karyotype to be deficient in a copy of a region of a chromosome as compared to the cell with the second karyotype at a particular chromosomal location, preferably the ratio of the first (eg green) and second (eg red) labels hybridised to the amplified DNA will be larger than 1.20 (ie ratio of red/green) for an autosome or larger than 1.25 (ie ratio of red/green) for a sex chromosome. Conversely, for the cell with the first karyotype to have an additional copy of a region of a chromosome as compared to the cell with the second karyotype at a particular chromosomal location, preferably the ratio of the first (eg green) and second (eg red) labels hybridised to the amplified DNA will be less than 0.80 (ie ratio of red/green) for an autosome or less than 0.75 (ie ratio of red/green) for a sex chromosome.

The present invention also provides a method of detecting a chromosomal abnormality in a cell with an unknown karyotype, the method including the steps of:
(a) amplifying DNA from an isolated chromosome or part of an isolated chromosome;
(b) attaching the amplified DNA to a solid substrate;
(c) amplifying DNA from one or more cells with an unknown karyotype and amplifying DNA from one or more cells with a reference karyotype;
(d) labelling the amplified DNA from the one or more cells with an unknown karyotype with a first label, and labelling the amplified DNA from the one or more cells with a reference karyotype with a second label, wherein the first and second labels are detectably different;
(e) hybridizing the amplified and labelled DNA from the one or more cells with an unknown karyotype to the amplified DNA attached to the solid substrate, and hybridizing the amplified and labelled DNA from the one or more cells with a reference karyotype to the amplified DNA attached to the solid substrate; and
(f) detecting the presence of a chromosomal abnormality in the cell with the unknown karyotype by comparing the relative amount of the first label hybridised to the amplified DNA attached to the solid substrate to the amount of second label hybridised to the amplified DNA attached to the solid substrate.

The chromosomal abnormality may be any change or alteration in a chromosome that may be detected by a method utilising comparative genomic hybridization. Examples of chromosomal abnormalities that may be detected by this form of the present invention include extra or missing individual chromosomes, extra or missing portions of a chromosome, breaks and chromosomal rearrangements such as translocations, dicentrics, inversions, insertions, amplifications, and deletions.

Preferably, the method of this form of the present invention is used for pre-implantation diagnosis of an embryo or an oocyte, or for the prenatal diagnosis of a foetus for a chromosomal abnormality.

In the case of an isolated chromosome, preferably the chromosome is isolated by microdissection or flow cytometry. In the case of part of an isolated chromosome, preferably the part of an isolated chromosome is a cloned fragment of a chromosome. Preferably, the DNA from a part of an isolated chromosome, or the amplified DNA from part of an isolated chromosome, is depleted of non-chromosomal sequences.

Preferably, the amplifying of DNA from an isolated chromosome or a part of an isolated chromosome is randomly primed amplification. More preferably the randomly primed amplification includes the use of a degenerate oligonucleotide primer. Most preferably, the degenerate oligonucleotide primer consists of the nucleotide sequence 5'-CCGACTCGAGNNNNNNATGTGG-3' (SEQ ID NO.1), wherein N is any nucleotide.

Preferably, the amplified DNA from an isolated chromosome or part of an isolated chromosome is depleted of repetitive sequences and/or sequences that over represented due to the amplifying of the DNA.

Preferably, the repetitive sequences are Cot-1 sequences.

Preferably, the amplified DNA from an isolated chromosome or part of an isolated chromosome is size selected prior to attaching to the solid substrate. More preferably, the amplified DNA from an isolated chromosome or part of an isolated chromosome is size selected for DNA of a size of less than 10 kb. Most preferably, the amplified DNA from the isolated chromosome or part of an isolated chromosome is size selected for DNA of a size of less than 3 kb.

Preferably, the amplifying of DNA from one or more cells with an unknown karyotype and the amplification of DNA from one or more cells with a reference karyotype is randomly primed DNA amplification. More preferably, the amplifying includes the use of a degenerate oligonucleotide primer. Most preferably, the degenerate oligonucleotide primer consists of the nucleotide sequence 5'-CCGACTCGAGNNNNNNATGTGG-3' (SEQ ID NO.1), wherein N is any nucleotide.

Preferably, the amplified DNA from one or more cells with an unknown karyotype and the amplified DNA from one or more cells with a reference karyotype are both depleted of repetitive sequences.

Preferably, the repetitive sequences are Cot-1 sequences.

The cell with the unknown karyotype may be any cell for which the presence of a chromosomal abnormality is to be screened. Examples of chromosomal abnormalities that may be amenable to detection by the present invention include Trisomy 21, 13 and 18 and the detection of missing, chromosomes, such as occurs in Turner's syndrome (45, XO).

The chromosome abnormality may be associated with any chromosome present in a cell of any ploidy (haploid, diploid or polyploid), including a sex chromosome, an autosome, a mitochondrial chromosome, a chloroplast chromosome or an episome. Preferably, the chromosome abnormality is present on a sex chromosome or an autosome. Most preferably, the chromosome abnormality is present on an autosome.

The cell with the unknown karyotype may be a eukaryotic or a prokaryotic cell. Preferably, the cell is a eukaryotic cell. More preferably, the cell is an animal or human cell. Most preferably, the cell is a human cell.

Preferably, the cell with the unknown karyotype is a foetal cell, a cell derived from an embryo (including a blastomere), a germ cell, a cancerous cell or any other type of somatic cell with a chromosomal abnormality to be screened. More preferably the cell with the unknown karyotype is a foetal cell, an embryonic cell or germ cell. Most preferably, the cell with the unknown karyotype is an embryonic cell or a germ cell.

Accordingly in a preferred form, the present invention also provides a method of detecting a chromosomal abnormality in an embryo or a germ cell, the method including the steps of:
(a) amplifying DNA from an isolated chromosome or part of an isolated chromosome;
(b) attaching the amplified DNA to a solid substrate;
(c) isolating a cell from an embryo or a germ cell;
(d) amplifying DNA from the cell isolated from an embryo or germ cell;
(e) amplifying DNA from one or more cells with a reference karyotype;
(f) labelling the amplified DNA from the cell isolated from an embryo or germ cell with a first label, and labelling the amplified DNA from the one or more cells with a reference karyotype with a second label, wherein the first and second labels are detectably different;
(g) hybridizing the amplified and labelled DNA from the cell isolated from an embryo or germ cell to the amplified DNA attached to the solid substrate, and hybridizing the amplified and labelled DNA from the one or more cells with a reference karyotype to the amplified DNA attached to the solid substrate; and
(h) detecting the presence of a chromosomal abnormality in the embryo or the germ cell by comparing the relative amount of the first label hybridised to the amplified DNA attached to the solid substrate to the amount of second label hybridised to the amplified DNA attached to the solid substrate.

In detecting a chromosomal abnormality, a large number of cells may not necessarily be associated with a more accurate determination of the presence of a particular chromosomal abnormality, and in some cases it may be preferable that a single cell or a relatively small number of cells is isolated.

Accordingly, in a preferred form, the present invention also provides a method of detecting a chromosomal abnormality in a single cell with an unknown karyotype, the method including the steps of:
(a) randomly amplifying DNA from an isolated chromosome or part of an isolated chromosome;
(b) attaching the amplified DNA to a solid substrate;
(c) randomly amplifying DNA from a single cell with an unknown karyotype and amplifying DNA from one or more cells with a reference karyotype;
(d) labelling the amplified DNA from the single cell with an unknown karyotype with a first label, and labelling the amplified DNA from one or more cells with a reference karyotype with a second label, wherein the first and second labels are detectably different;
(e) hybridising the amplified and labelled DNA from the single cell with an unknown karyotype to the amplified DNA attached to the solid substrate, and hybridising the amplified and labelled DNA from the one or more cells with a reference karyotype to the amplified DNA attached to the solid substrate; and
(f) detecting the presence of a chromosome abnormality in the single cell with the unknown karyotype by comparing the relative amount of the first label hybridised to the amplified DNA attached to the solid substrate to the amount of a second label hybridised to the amplified DNA attached to the solid substrate.

The cell with the reference karyotype may be any cell for which the karyotype of the cell with the unknown karyotype is to be compared. Preferably, the cell with the reference karyotype is from the same species as the cell with the unknown karyotype and also of the same type or a similar type as the cell with the unknown karyotype.

Preferably, the one or more cells with a reference karyotype is a cell of the same type as the one or more cells with an unknown karyotype.

The number of cells to be analysed in this form of the present invention is not particularly limited, and may range from a single cell (for example isolated from an embryo) to a large number of cells (for example isolated from a tissue biopsy or blood). For example, the method of the present invention may be applied to PGD on a single cell isolated from an embryo or a polar body from an oocyte, prenatal diagnosis of foetal cells, or the determination of the presence of a chromosomal abnormality in cancer cells or other somatic cells isolated from a subject by biopsy or isolated from the blood.

In the case of pre-natal diagnosis, for example, the number of cells to be analysed is also not particularly limited, and is preferably less than 500 cells, more preferably less than 400 cells and most preferably less than 100 cells, A suitable range is 50-400 cells.

Preferably, the amplified DNA from one or more cells with an unknown karyotype is DNA amplified from 1 to 20 cells. In a preferred form of the invention, the cell to be analysed is a single cell or a small number of cells, being in the range from 2 to 20 cells.

Preferably, the number of cells from which DNA is to be extracted and amplified is the same or similar between the cell or cells with the unknown karyotype and the cell or cells with the reference karyotype. For example, in the case of PGD on a single cell from an embryo or the polar body from an oocyte, a single cell from another source will be preferably used for the comparison.

In one embodiment, it may also be desired to detect a specific chromosomal abnormality in the cell with an unknown karyotype with the same region in a cell with a reference karyotype. In this form, a specific primer or a set of specific primers may be added to the extracted DNAs from both the cell with the unknown karyotype and the cell with the reference region.

The specific primer or the set of specific primers may be added to other primers that are present in the reaction mix for the purposes of, for example, randomly amplifying the extracted genomic DNA. Alternatively, the specific primer or the set of specific primers may be used as the only primers to amplify the extracted DNA.

Examples of primers that may be used to detect a chromosomal abnormality in a specific region are primers that amplify a specific region of a small chromosome (eg chromosomes 21 and 22). In such a case, it may be preferable to add such primers to a set of primers that randomly amplify the genomic DNA, such as DOP primers.

In the situation where it is desired to amplify a specific chromosomal region, a specific locus, or one or more specific genes associated with a chromosomal abnormality, primers to the particular region may be used alone or in combination with other primers, such as DOP primers to randomly amplify genomic DNA. For example, chromosomal regions including the regions involved in diseases such as thalassemia, Duchenne muscular dystrophy, X-linked disorders and Haemophilia may be amplified for analysis of chromosomal abnormalities. It will be appreciated in this regard that the method of the current invention is useful for the detection of major chromosomal abnormalities such as deletions and multiplications, and the specific loci being amplified will need to carry such abnormalities to allow their detection by the method of the present invention.

Thus, the amplification of DNA from one or more cells with an unknown karyotype and the amplification of DNA from one or more cells with a reference karyotype may also include amplification of the same specific chromosomal region.

The amplified DNA from the one or more cells with the unknown karyotype will be labelled with a first label, and the amplified DNA from one or more cells with the reference karyotype will be a labelled with a second label that is detectably different from the first label, Examples of detectably different labels for incorporation into DNA include SpectrumGreen-dUTP and SpectrumRed-dUTP (both from Vysis), or Cy3-dUTP and Cy5-dUTP.

The comparison of the relative amount of the first and second labels hybridised to the amplified DNA attached to the solid substrate may be used to detect whether the cell with the unknown karyotype has a chromosomal abnormality at a particular chromosomal position as the cell with the reference karyotype.

For the detection of a deficiency in a copy of a region of a chromosome, preferably the ratio of the first (eg green) and second (eg red) labels hybridised to the amplified DNA will be larger than 1.20 (ie ratio of red/green) for an autosome or larger than 1.25 (ie ratio of red/green) for a sex chromosome. Conversely, for the detection of an additional copy of a region of a chromosome, preferably the ratio of the first (eg green) and second (eg red) labels hybridised to the amplified DNA will be less than 0.80 (ie ratio of red/green) for an autosome or less than 0,75 (ie ratio of red/green) for a sex chromosome.

In another preferred form, the present invention provides a method of pre-implantation genetic diagnosis of an embryo, the method including the steps of:
(a) randomly amplifying DNA from an isolated chromosome or part of an isolated chromosome;
(b) attaching the amplified DNA to a solid substrate;
(c) randomly amplifying DNA from a cell from one or more embryonic cells with an unknown karyotype and amplifying DNA from one or more cells with a reference karyotype;
(d) labelling the amplified DNA from the one or more embryonic cells with an unknown karyotype with a first label, and labelling the amplified DNA from one or more cells with a reference karyotype with a second label, wherein the first and second labels are detectably different;
(e) hybridising the amplified and labelled DNA from the one or more cells with an unknown karyotype to the amplified DNA attached to the solid substrate, and hybridising the amplified and labelled DNA from the one or more cells with a reference karyotype to the amplified DNA attached to the solid substrate;
(f) detecting the presence of a chromosome abnormality in the embryo with the unknown karyotype by comparing the relative amount of the first label hybridised to the amplified DNA attached to the solid substrate to the amount of a second label hybridised to the amplified DNA attached to the solid substrate; and
(g) determining the suitability of the embryo or the oocyte for implantation by the absence of a chromosomal abnormality in the one or more embryonic cells.

In another preferred form, the present invention provides a method of pre-implantation genetic diagnosis of an oocyte, the method including the steps of:
(a) randomly amplifying DNA from an isolated chromosome or part of an isolated chromosome;
(b) attaching the amplified DNA to a solid substrate;
(c) randomly amplifying DNA from a polar body of an oocyte with an unknown karyotype and amplifying DNA from one or more cells with a reference karyotype;
(d) labelling the amplified DNA from the polar body of an oocyte with an unknown karyotype with a first label, and labelling the amplified DNA from one or more cells with a reference karyotype with a second label, wherein the first and second labels are detectably different;
(e) hybridising the amplified and labelled DNA from the polar body of an oocyte with an unknown karyotype to the amplified DNA attached to the solid substrate, and hybridising the amplified and labelled DNA from the one or more cells with a reference karyotype to the amplified DNA attached to the solid substrate;
(f) detecting the presence of a chromosome abnormality in the polar body of an oocyte with the unknown karyotype by comparing the relative amount of the first label hybridised to the amplified DNA attached to the solid substrate to the amount of a second label hybridised to the amplified DNA attached to the solid substrate, and
(g) determining the suitability of the oocyte for implantation by the absence of a chromosomal abnormality in the polar body of the oocyte.

In another preferred form, the present invention provides a method of prenatal diagnosis of a foetus for a chromosomal abnormality, the method including the steps of:
(a) randomly amplifying DNA from an isolated chromosome or part of an isolated chromosome;
(b) attaching the amplified-DNA to a solid substrate;
(c) randomly amplifying DNA from one or more foetal cells with an unknown karyotype and amplifying DNA from one or more cells with a reference karyotype;
(d) labelling the amplified DNA from the one or more foetal cells with an unknown karyotype with a first label, and labelling the amplified DNA from one or more cells with a reference karyotype with a second label, wherein the first and second labels are detectably different;
(e) hybridising the amplified and labelled DNA from the one or more foetal cells with an unknown karyotype to the amplified DNA attached to the solid substrate, and hybridising the amplified and labelled DNA from the one or more cells with a reference karyotype to the amplified DNA attached to the solid substrate; and
(f) determining the presence of a chromosome abnormality in the foetus by comparing the relative amount of the first label hybridised to the amplified DNA attached to the solid substrate to the amount of a second label hybridised to the amplified DNA attached to the solid substrate.

The present invention also provides a nucleic acid attached to a solid substrate, wherein the nucleic acid is derived from an isolated chromosome or part of an isolated chromosome and the nucleic acid is depleted of repetitive sequences.

This form of the present invention provides a nucleic acid attached to a solid substrate that is useful not only for comparative genomic hybridization, but is also useful as a target for detecting nucleic acids in any hybridization based system.

In the case of an isolated chromosome, preferably the chromosome is isolated by microdissection or flow cytometry.

In the case of part of an isolated chromosome, preferably the part of a chromosome is isolated by microdissection or flow cytometry, or is a cloned fragment of a chromosome.

The nucleic acid attached to the solid substrate may be any nucleic acid that is derived from an isolated chromosome or part of an isolated chromosome. The nucleic acid may be derived directly from the isolated chromosome or part of an isolated chromosome. For example, DNA from one or more isolated chromosomes may be depleted of repetitive sequences and directly attached to a solid substrate, or the DNA from one or more clones containing genomic DNA may be depleted of repetitive sequences and directly attached to the solid substrate.

Alternatively, the nucleic acid attached to the solid substrate may be the product of amplification of an isolated chromosome or part of an isolated chromosome.

Preferably, the nucleic acid attached to the solid substrate is the product of amplification of the DNA from an isolated chromosome or part thereof. Once again, the repetitive sequences may be depleted from the DNA before amplification, or alternatively, after amplification.

In the case of amplification of the DNA from an isolated chromosome or part of an isolated chromosome, preferably the amplification will result in the amplification of substantially the entire target. Accordingly, it is preferred that the amplification of the isolated chromosome or a part of the isolated chromosome is randomly primed amplification.

Accordingly, in a preferred form the present invention provides a nucleic acid attached to a solid substrate, the nucleic acid being derived from randomly primed amplification of an isolated chromosome or part of an isolated chromosome, wherein the nucleic acid is depleted of repetitive sequences.

Amplification of the DNA from an isolated chromosome or part of the isolated chromosome will be performed with one or more appropriate primers. As discussed above, preferably the one or more primers used will result in the random amplification of the DNA of the isolated chromosome or part of the isolated chromosome.

Preferably, the one or more primers used is an oligonucleotide including one or more nucleotides of random sequence. More preferably, the one or more primers is an oligonucleotide including one or more contiguous nucleotides of random sequence. More preferably, the one or more of primers is an oligonucleotide that includes six or more contiguous nucleotides of random sequence, such as a DOP primer (degenerate oligonucleotide primer). Most preferably, the one or more primers is a primer with the following nucleotide sequence:

5'-CCGACTCGAGNNNNNNATGTGG-3'.   (SEQ ID NO. 1)

where NNNNNN represents the degenerate sequence. "N" is any nucleotide ie N represents the four possible nucleotides in the DNA sequence: "A", "T", "G" and "G" for Adenine, Thymine, Cytosine and Guanine, respectively. As such, the degenerate sequence contain mixtures of various nucleotide sequences including all possible combinations of A, T, C and G at the "N" positions.

If so desired, the nucleotide sequence of the degenerate sequence can also be biased towards a particular nucleotide composition, for example GC or AT richness.

In the case of amplification using DOP primers on an isolated chromosome, or a part of a chromosome isolated by microdissection, the amplification may be performed essentially as described in Telenius et al. (1992) *Genomics* 18:718-725. Briefly, the amplification is performed under low stringency conditions for a low number of cycles (eg five cycles) and a second stage amplification performed under more stringent conditions for a larger number of cycles (eg 35 cycles).

Alternatively, random primed amplification may be achieved using one or more primers of fixed sequence and performing a low number of cycles of amplification under low stringency conditions that allow the one or more primers to prime synthesis randomly throughout the target, followed by a second stage amplification performed under more stringent conditions for a larger number of cycles.

In addition, to account for regions of small chromosomes that may present a difficulty in achieving randomly primed amplification, region specific primers can be used in conjunction with other primers that allow random amplification. For example, primers to specific regions of chromosomes 21 and 22 may be used in conjunctions with DOP primers.

Other suitable techniques for amplification of the isolated chromosome or part of an isolated chromosome include primer-extension pre-amplification PCR (PEP-PCR) which may be performed essentially as described in Zhang et al. (1992) *Proc Natl. Acad. Sci* 89:5847-5851); ligation mediated PCR, which may be performed essentially as described in Klein et al. (1999) *Proc. Natl. Acad. Sci.* 96:4494-4499); or alu-PCR, which may be performed essentially as in Nelson et al. (1989) *Proc. Natl. Acad. Sci.* 86:6686-6690).

In the case of using rolling circle amplification on a cloned genomic insert in a circular vector, rolling circle amplification may be performed using suitable conditions known in the art, such as described in Fire, A. and Xu, S-Q. (1995) *Proc. Natl. Acad. Sci* 92:4641-4645.

A number of methods known in the art can be used to deplete the amplified DNA of repetitive sequences.

As discussed previously, repetitive sequences may be removed either prior to amplification or after amplification. For example, chromosomal DNA may be isolated and repetitive sequences removed. Alternatively, the DNA may first be amplified with appropriate primers and the repetitive DNA sequences removed from the amplified pool of nucleic acids.

Examples of repetitive sequences include simple repeated DNA (eg Alu or Kpn elements), satellite repeats, mini-satellite repeats, chromosome-specific repeats, micro-satellite repeats, repeated genes (eg rRNA genes), sequences derived from transposable elements (eg transposons with DNA or RNA intermediates), elements derived from multiple copies of viruses such as retroviruses, repeats associated with centromeres or telomeres, or repeats associated with heterochromatin.

A number of methods known in the art can be used to remove repetitive sequences For example, in many genomes, such as the human genome, a major portion of repetitive DNA is contained in a few families of highly repeated sequences such as Alu. To remove such repetitive sequences, a blocking procedure can be used. These methods primarily exploit the fact that the hybridization rate of complementary nucleic acid strands increases as their concentration increases. Thus, if a mixture of nucleic acid fragments is denatured and incubated under conditions that permit hybridization, the sequences present at high concentration will become double-stranded more rapidly than the others. The double-stranded nucleic acid can then be removed by the direct removal of these sequences by a method known in the art.

For example, single- and double-stranded nucleic adds have different binding characteristics to hydroxyapatite. Such characteristics provide a basis commonly used for fractionating nucleic acids. The fraction of genomic DNA containing sequences with a particular degree of repetition can be obtained by denaturing genomic DNA, allowing it to reassociate under appropriate conditions, followed by separation using hydroxyapatite. Such techniques are as described in Britten et al. "Analysis of Repeating DNA Sequences by Reassociation" *Methods in Enzymology* 22: 363-418 (1974).

Examples of such sequences that can be used to deplete the amplified DNA of repetitive sequences include human Cot-1 DNA and Alu—repeat containing DNAs.

Alternatively, reaction with immobilized nucleic acid may be performed. For example, minimally sheared human genomic DNA is bound to diazonium cellulose or a like support. The amplified DNA, appropriately cut into fragments, is hybridized against the immobilized DNA to Cot values in the range of about 1 to 100. The material that does not bind to the immobilised nucleic acid may then be attached to the solid substrate.

In a preferred embodiment, the nucleic acid derived from the isolated chromosome or part thereof to be attached to the solid substrate is further depleted of non-chromosomal sequences.

Non-chromosomal sequences are sequences that are not normally present in the nucleotide sequence of the chromosome or part thereof, such as sequences derived from a vector or plasmid, or contaminating sequences that may be present in the originally target sample to be amplified, such as bacterial sequences (eg sequences derived from *E.coli*). Sequences that are over-represented due to amplification of the chromosome are sequences present after amplification of the target that have been disproportionately amplified in comparison to other sequences normally present in the target.

Non-chromosomal sequences may be depleted as described previously. In the case of depleting non-chromosomal sequences from amplified nucleic acid, non-chromosomal sequences may be depleted by using non-chromosomal sequences in excess in a hybridization reaction with the target or the amplified DNA, or by attaching the non-chromosomal sequences to a solid support and using theses sequences to deplete the DNA of these sequences.

In another preferred embodiment, randomly amplified nucleic acid derived from the. isolated chromosome or part thereof that is to be attached to the solid substrate may be further depleted of sequences that are over-represented due to amplification.

In the case of depleting over-represented sequences due to amplification, the target sequences may be depleted from the target before amplification by similar methods described above, or the over-represented amplified sequences may be depleted after amplification. As will be appreciated, identification of the actual sequence being over-represented is necessary, and will depend on the primers being used and the nature of the target to be amplified.

Over represented sequences and repetitive sequences may be depleted together by amplifying a source of repetitive sequences with the same primers used to amplify the DNA from an isolated chromosome or part of an isolated chromosome. The amplified repetitive nucleic acid can then be used to deplete the amplified DNA of over represented and repetitive sequences. For example, DOP-PCR may be performed on Cot-1 DNA, and the resultant amplification products used to deplete the amplified DNA from an isolated chromosome or part of an isolated chromosome.

In a preferred form, the present invention also provides a nucleic acid attached to a solid substrate, wherein the nucleic acid is derived from randomly primed amplification of an isolated chromosome or part of an isolated chromosome and the nucleic acid is depleted of one or more of repetitive sequences, non-chromosomal sequences or sequences that are over-represented due to amplification of the chromosome or part of the isolated chromosome.

The nucleic acid from the isolated chromosome or part of the isolated chromosome may also subjected to size selection before attachment to the solid substrate. Preferably, the amplified nucleic add attached to the solid substrate is less than 10 kb in size. More preferably, the amplified nucleic acid attached to the solid substrate is less than 3 kb in size.

Size selection may be performed by a suitable method known in the art. For example, the amplified nucleic acid may be electrophoresed on an agarose gel, and DNAs with a size in the range from 150 to 3000 bp may be isolated.

In a preferred form, the nucleic add attached to the solid substrate is the product of randomly primed amplification of an isolated chromosome or part of an isolated chromosome, wherein the nucleic acid has been size selected.

In this case, the randomly amplified nucleic acid attached to the solid substrate is preferably less than 10 kb in size. More preferably, the randomly amplified nucleic acid attached to the solid substrate is less than 3 kb In size. For example, randomly amplified DNA may be electrophoresed on an agarose gel, and DNAs with a size in the range from 150 to 3000 bp may be isolated.

The nucleic acid may be attached to a solid substrate by a suitable method known in the art, including passive adsorption or covalent linkage. For example, amplified DNA may be attached to a glass substrate by passive adsorption by spotting samples onto a Polysine™ microscope glass slide (Menzel-Glaser, Germany) and processing of the slide by dehydration, snap-drying, fixation through UV cross linking, and chemical blocking by using succinic anhydride. In the case of covalent linkage, the nucleic acid may be attached to the solid substrate by a suitable method known in the art.

It is preferred that more than one nucleic acid is attached to the solid substrate, to produce an array of deposited nucleic acids. Such an array can be manufactured in any desired manner known in the art, including robotic deposition of the nucleic acids. Examples of methods for producing arrays are essentially as described in U.S. Pat. Nos. 5,486,452, 5,830,645, 5,807,552, 5,800,992 and 5,445,934.

Accordingly, in a preferred form, the present invention also provides an array of nucleic acids attached to a solid substrate, wherein each nucleic acid in the array is derived from an isolated chromosome or part of an isolated chromosome and each nucleic acid is depleted of repetitive sequences.

In another preferred form, the present invention also provides an array of nucleic acids attached to a solid substrate, wherein each nucleic acid in the array is the product of randomly primed amplification of an isolated chromosome or part of an isolated chromosome and each nucleic acid is depleted of one or more of repetitive sequences, non-chromosomal sequences or sequences that are over-represented due to amplification of the chromosome or part thereof.

It will also be appreciated that the array may not necessarily be composed of nucleic acids according to the present invention, but in addition to the one or more nucleic acids attached to a solid substrate according to the present invention, may also include other target nucleic acids.

Any suitable amount of nucleic acid may be deposited on the solid substrate. The amount of nucleic acid deposited can be from about 0.05 nl to about 5.0 nl of a nucleic acid solution of 0.15-1 µg/µl nucleic acid concentration. For example, for a density of 1,000 DNAs deposited/cm, the individual amount deposited is about 0.2 nl to about 2.0 nl of 1 µg/µl solution. The DNA is provided in any solvent that will permit deposition of the nucleic acid.

The array having deposited nucleic acids may be produced in any arrangement. For example, the nucleic acids can be located in one portion of the array or can be interspersed among other deposited nucleic acids. The regularity of a two dimensional array is preferred.

It is also preferred that the array include various control nucleic acids, such as, for example, spotted nucleic acids of known copy number for a particular expressed gene or genomic sequence. For example, genomic DNA extracted from cell lines with 1 or more copies of a particular chromosome can be used, or the entire DOP-PCR products of amplification of DNA from a single cell can also be used.

In another form, the present invention also provides a kit for comparing at least one chromosome or part thereof from a cell with a first karyotype with the corresponding chromosome or part thereof from a cell with a second karyotype, the kit including a nucleic acid attached to a solid substrate, wherein the nucleic acid is derived from an isolated chromosome or part of an isolated chromosome and the nucleic add is depleted of repetitive sequences.

In a further form, the present invention also provides a kit for comparing at least one chromosome or part thereof from a cell with a first karyotype with the corresponding chromosome or part thereof from a cell with a second karyotype, the kit including a nucleic acid attached to a solid substrate, wherein the nucleic acid is the product of randomly primed amplification of an isolated chromosome or part of an isolated chromosome and the nucleic acid is depleted of one or more of repetitive sequences, non-chromosomal sequences or sequences that are over-represented due to amplification.

The various kits of the present invention are also suitable for detecting a chromosomal abnormality in a cell.

Accordingly, in another form, the present invention also provides a kit for detecting a chromosomal abnormality in a cell with an unknown karyotype, the kit including a nucleic acid attached to a solid substrate, wherein the nucleic acid is derived from an isolated chromosome or part of an isolated chromosome and the nucleic acid is depleted of repetitive sequences.

In a further form, the present invention also provides a kit for detecting a chromosomal abnormality in a cell with an unknown karyotype, the kit including a nucleic acid attached to a solid substrate, wherein the nucleic acid is the product of randomly primed amplification of an isolated chromosome or part of an isolated chromosome and the nucleic acid is depleted of one or more of repetitive sequences, non-chromosomal sequences or sequences that are over-represented due to amplification of the chromosome or part thereof.

The present invention also provides a nucleic acid derived from randomly primed amplification of an isolated chromosome or part of an isolated chromosome, wherein the nucleic acid is depleted of repetitive sequences.

The nucleic acids of this form of the present invention may be used as target nucleic acids for hybridisation, and in particular, as target nucleic acids for comparative genomic hybridisation.

Preferably, the nucleic acids are derived from randomly primed amplification that includes the use of a degenerate oligonucleotide primer. More preferably, the nucleic acids are derived from randomly primed amplification that includes the use of a degenerate oligonucleotide primer that consists of the nucleotide sequence 5'-CCGACTCGAGNNNNNNNAT-GTGG-3' (SEQ ID NO.1), wherein N is any nucleotide.

In the case of a nucleic acid derived from amplification of an isolated chromosome, the isolated chromosome is preferably isolated by microdissection or flow cytometry, In the case of a nucleic add derived from amplification of part of an isolated chromosome, the part of the chromosome may be isolated by microdissection or flow cytometry. Alternatively, the part of the isolated chromosome may be a cloned fragment of a chromosome. In this case, preferably the randomly primed amplified nucleic acid from the cloned genomic fragment will be depleted of non-chromosomal sequences.

Preferably, the nucleic acid is further depleted of sequences that are over represented due to amplification.

Preferably, the repetitive sequences are Cot-1 sequences.

The nucleic add may also be size selected. Preferably, the nucleic acid is size selected for a size of less than 10 kb. More preferably, the nucleic add is size selected for a size of less than 3 kb.

In a preferred form, the present invention also provides a nucleic acid derived from randomly primed amplification of an isolated chromosome or part of an isolated chromosome, wherein the nucleic acid is depleted of repetitive sequences and the nucleic acid is size selected.

Description of the Preferred Embodiments

Reference will now be made to experiments that embody the above general principles of the present invention. However, it is to be understood that the following description is not to limit the generality of the above description.

EXAMPLE 1

Human Chromosome-Specific DNA Libraries

A complete set of repeat-depleted, PCR-amplifiable, human chromosome-specific painting probes was kindly provided by Drs. A. Bolzer and M. R. Speicher (Institut für Anthropologie and Humangenetik, LMU München, München, Germany).

Because of their ability to uniformly paint the whole target chromosome (arms), these probes were selected in this project as DNA libraries of human chromosomes. The DNA libraries were generated by microdissection for 15 chromosomes of No. 1, 3, 6, 7, 9, 12, 13, 14, 15, 17, 19, 20, 21, 22, and X) or flow-sorting for 9 chromosomes of No. 2, 4, 5, 8, 10, 11, 16, 18, and Y. In order to avoid cross-hybridization among the p arms of five acrocentric chromosomes (13~15, 21, and 22), only q arms of these chromosomes were microdissected into their corresponding DNA libraries (Guan et al. (1994) *Genomics* 22:101-107).

Using subtracters including human Cot-1 DNA, chromosome centromere-specific probes, and aphoid region-specific probes, further depletion of repetitive sequences out of these probes was successfully conducted by affinity chromatography. Briefly, repeat sequences were labelled with biotin and allowed to hybridise to the library containing repeat sequences. After hybridization streptavidin-magnetic bead affinity chromatography was used to remove the repeat sequences bound to the biotin labelled repeat sequences. Without addition of human Cot-1 DNA to suppress repetitive sequences, these repeat-depleted DNA libraries achieve high specific FISH signals on their corresponding target chromosomes (q arms) as described in Craig et al. (1997) *Hum. Genet.* 100:472-474 and Bolzer et al, (1999) *Cytogenet. Cell Genet.* 84:233-240.

EXAMPLE 2

Preparation of Human Chromosome-Specific DNA Libraries

Successful re-amplification of the human DNA library described in Example 1 was achieved by single round of degenerate oligonucleotide-primed PCR (DOP-PCR) for 30-35 cycles of high-stringent cycling conditions, essentially as described in Telenius et al. (1992) Genomics 13:718-725.

Briefly, amplification was carried out in a Minicycler (MJ Research, USA) in a volume of 50 μl, which contained about 50~100 ng of source probes, Taq DNA ploymerase buffer (50 mM KCl, 10 mM Tris-HCl [pH 8.3], Perkin Elmer, USA), 2.0 μM primer 6MW(5'-CCGACTCGAGNNNNNNATGTGG-3' (SEQ ID NO.1), 2.5 mM $MgCl_2$, 0.25mM of each dNTP, and 5 U Taq DNA polymerase (Perkin Elmer, USA). After an initial denaturation step of 95° C. for 4 min, 30-35cycles were followed using cycling conditions of 94° C. for 1 min, 62° C. for 1 min, and 72° C. for 3 min with an addition of 10 seconds per cycle to the extension time. Finally an extension step of 72° C. for 10 min was added at the end of cycling amplification.

5 μl of PCR products was electrophoresed on 1% agarose gels in 0.5×TBE (Tris, borate, EDTA) prestained with ethidium bromide and photographed. The results are shown in FIG. 1.

As can be seen, successful amplification of the whole set of repeat-depleted human chromosome-specific DNA libraries was achieved by one round of DOP-PCR amplification of 30-35 cycles by using the high stringent cycling conditions of the traditional DOP-PCR. All PCR products of reamplified DNA libraries were smears with the majority less than 1 kb after 30 min run on 1% Agarose gels. However, differences of smears were obvious. Wider smears extending up to more than 3 kb were seen for products of eleven different chromosomes (No. 1, 2, 4, 5, 8, 9, 10, 11, 16, 21, and Y), only three of which were microdissection-derived probes (No. 1, 9, and 21).

Comprehensively optimising the cycling conditions of DOP-PCR, which included both temperature and duration for both steps of annealing and elongation, the numbers of amplification cycles, initial DNA quantities of templates, and salt concentrations of $MgCl_2$, failed to remove the differences in sizes of the PCR products.

Purification of the PCR products was then conducted by Ultrapure PCR purification kits(#12500-250, Mo Bio Laboratories, Inc., CA, USA). Purified products were either used immediately or stored at −20° C. for one year without any visible loss of their specificities, as determined by FISH signals.

EXAMPLE 3

Fluorescence In Situ Hybridization Using Re-Amplified DNA Libraries

FISH experiments were carried out to confirm the specificities for the DNA libraries of human chromosomes reamplified by using metaphase chromosomes of peripheral lymphocytes from a normal human male.

Fluorescence in situ hybridization was carried out as follows:

SpectrumGreen-dUTP or SpectrumRed-dUTP (Vysis, USA) was used to label the amplified DNA libraries. Labelling reaction was carried out in a Minicycler (MJ Research, USA) with a volume of 50 μl using similar DOP-PCR cycling conditions used above to reamplify source probes of DNA libraries (Example 2). Low concentration of dNTP was the only exception employed here with 0.16 mM for each of dGTP, dCTP, and dATP, and 0.12 mM for dTTP with addition of 0.04 mM for either SpectrumGreen-dUTP or Spectrum-Red-dUTP. Purification of PCR products was conducted by Ultrapure PCR purification kits(#12500-250, Mo Bio Laboratories, Inc., CA, USA). For FISH experiments, 1 μg of purified labelled products was mixed with 20 μg of human Cot-1 DNA(GIBICO, BRL) and 50 μg of Salmon sperm DNA (GIBICO, BRL). The probe mixture was precipitated with ethanol and resuspended in 10 μl of hybridization solution, which was consisted of 50% deionized formamide, 3×SSC, 0.1% SDS, 10% dextran sulfate, and 5× Denhardt's solution.

After denaturation at 80° C. for 10 min and preannealing at 37° C. for 30 min, probes were hybridized to denatured metaphase chromosome spreads at 37° C. overnight. After hybridization, the slides were washed twice with 2×SSC at 60° C. for 10 min and then twice with 0.1×SSC at 60° C. for 5 min. After that, slides were further washed once in 0.1×SSC at room temperature for 5 min and then briefly rinsed in $H_2O$ for a few seconds. After being dried by air in the dark, slides were counterstained with 40 μl of DAPI solution containing antifading medium and covered with coverslips sealed by nailsticks. FISH signals were obtained and photographed by microscope of AHBT3(Olympus, Tokyo, Japan) using (1) excitation with blue for Green signals and (2) excitation Triple for Red signals.

Figure 2:
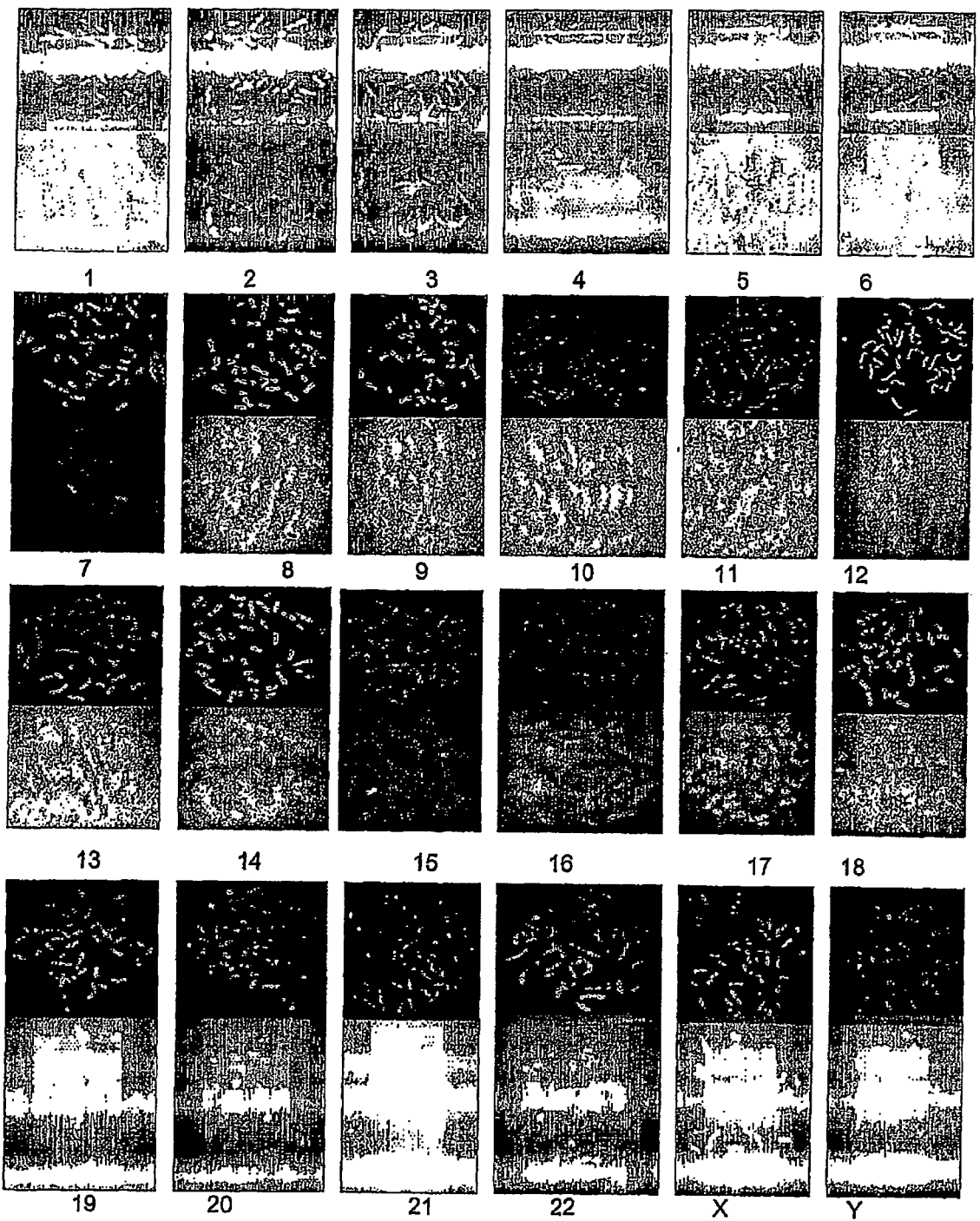
FIG. 2 shows FISH results of reamplified DNA libraries of human chromosomes, as described in Example 3. FISH was carried out using metaphase chromosome spreads of lymphocytes from normal male peripheral blood. Either SpectrumGreen-dUTP or SpectrumRed-dUTP was used to label DNA probes by DOP-PCR amplification. Except for very faint signals for the DNA library of chromosome 21, all the others uniformly painted their whole target chromosomes or q arms.

As shown in FIG. 2, except for very faint signals for the DNA library of chromosome 21, all the others uniformly painted their whole target chromosomes or q arms.

EXAMPLE 4

Manufacture of DNA Arrays (i) DNA Arrays of PCR Amplified Libraries of Human Chromosomal DNA (First Generation Array)

DNA arrays were made using the Microarray facilities of the University of Adelaide, South Australia.

Briefly, all re-amplified DNA libraries of human chromosomes were resuspened in spotting buffer of 3×SSC with final DNA concentration of around 100 ng/μl, and then 8 μl of each suspension solutions were loaded into the wells of a 384-well plate. Subsequently, a microarrayer sampled wells from this plate and spotted 8 replicates for every DNA sample on Polysine™ microscope glass slides (Menzel-Glaser, Germany). Post-processing of the printed array slides included dehydration, snapping-dry, fixation through UV cross linking, and chemical blocking by using succinic anhydride. Finally, after being dried by centrifuging at 500 rpm for 5 min. array slides could be used immediately or stored in slide box for a short period of time in the dark.

Figure 3:
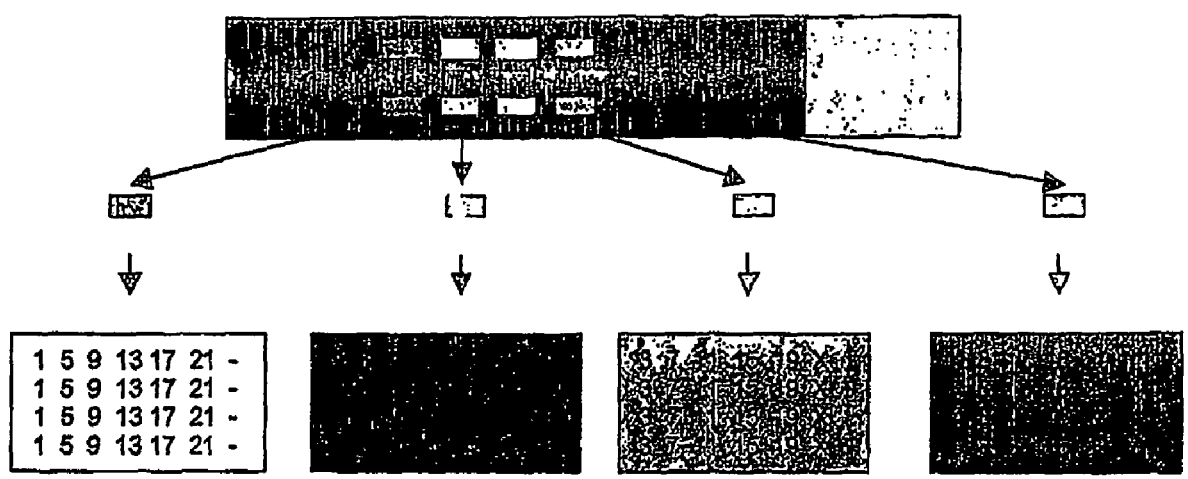
FIG. 3 shoves a depiction of the expected DNA array format by using loading of a 384-well-plate, as described in Example 4.

Thirty array slides were manufactured. As shown in FIG. 3, two replicate arrays were spotted on every slide. Each array had 4 blocks. Within each array four blocks were referred from left to right as the $1^{st}$, $2^{nd}$, $3^{rd}$, and $4^{th}$ block, which had 7, 7, 6, and 6 columns, respectively. Each column was consisted of 4 replicates of one DNA library of a single human chromosome. From left to right, their column's orders corresponding to DNA libraries of human chromosomes were No. 1-5-9-3-17-21-negative, No. 2-6-10-14-18-22-positive, No. 3-7-11-15-19-X-blank, and No. 4-8-12-16-20-Y-blank for the $1^{st}$, $2^{nd}$, $3^{rd}$, and $4^{th}$ block, respectively.

(ii) DNA Arrays of PCR Amplified Libraries of Human Chromosomal DNA after Size Selection (Second Generation Array)

Figure 4:
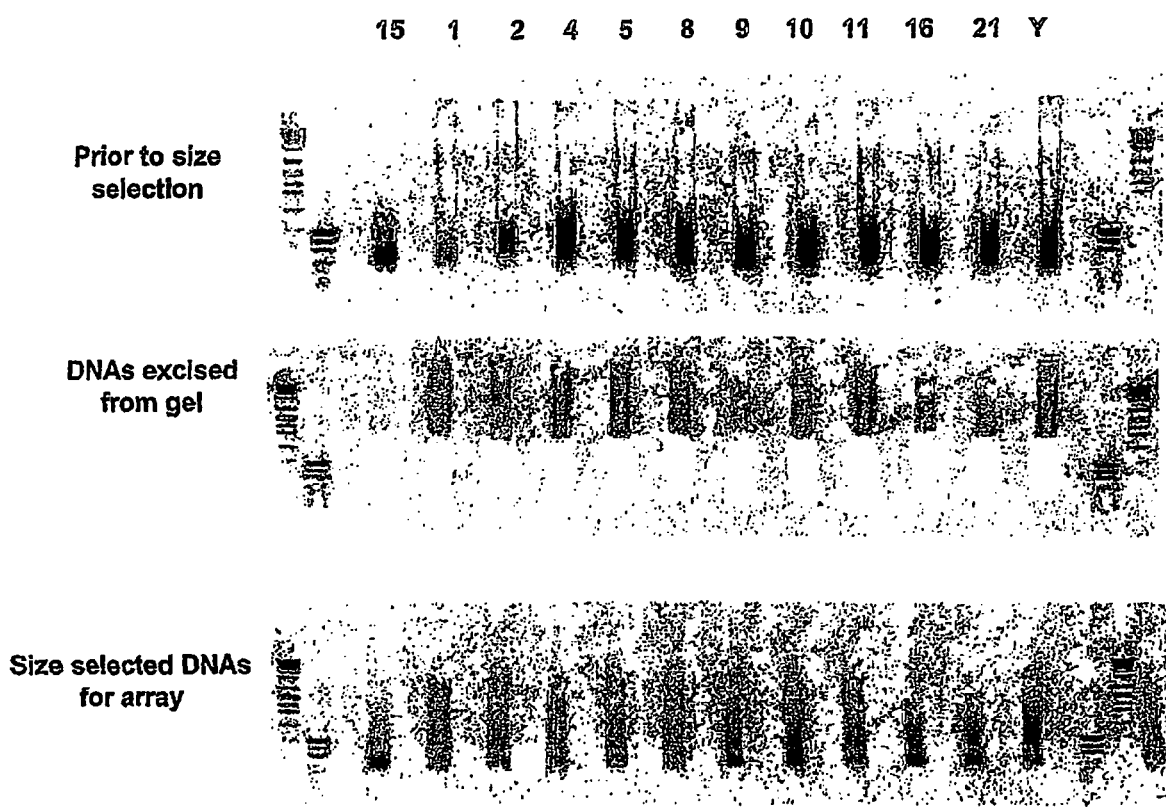
FIG. 4 shows results of electrophoresis of re-amplified DNA libraries before, during and after size selection, as described in Example 4(ii) for the manufacture of second generation arrays.

A DNA array with size selected products was produced by electrophoresis of the re-amplified DNA libraries described in Example 2 on a 1% Agarose gel. After staining, DNAs in the size range of 150-3000 bp were excised from the gel and isolated, as shown in FIG. 4.

The resulting size selected DNAs were then spotted onto an array along with the original DNA libraries prior to size selection as described previously, with the following changes: DNA was resuspended in 150 mM sodium phosphate, pH 8.0 at an approximate concentration of 170 ng/μl. An amount of approximately 0.6 nl was spotted for each spot using Stealth Micro Spotting Pins (Catalogue SMP3) from TeleChem. The slides used were SuperAmine slides from TeleChem (Sunnyvale, Calif.) which were used straight from the box. The Arraying facility which performed the microarraying was the Clive & Vera Ramaciotti Centre for Gene Function Analysis microarray facility located at the University of New South Wales which uses a ChipWriter Pro (Bio-Rad) microarrayer.

EXAMPLE 5

Isolation and Preparation of Single Cells

Single lymphocytes isolated from normal male or normal female peripheral blood were used as reference cells, and single amniocytes from amniocyte cell cultures of pregnancies of trisomies 13 and 18 were used as test cells. Cytogenetic analysis was used to confirm the normal karyotypes of the 46, XX and 46, XY reference samples. Using an inverted light microscope and finely pulled glass pipettes, single cells were selected and transferred into 0.5 ml PCR tubes essentially as described in Hussey at al. (1999) *Mol. Hum. Reprod.* 5:1089-1094, which could be used immediately or frozen for a period of time.

EXAMPLE 6

First Round DOP-PCR for Random Amplification

Lysis of single cells was achieved by 5 μl of lysis buffer (200 mM KOH, 50 mM dithiothreitol) for 10 min at 65° C. followed by neutralization with 5 μl of neutralization buffer (300 mM KCl, 900 mM Tris-HCl, Ph 8.3, 200 mM HCl). To the 10 μl of lysed and neutralized solution of single cells was added: 5 μl of K$^+$-free PCR buffer (100 mM Tris-HCl, pH 8.3, gelatin 1 mg/ml), 5 μl of 25 mM MgCl$_2$, 4 μl of 2.5 mM of each dNTP, 5 μl of 20 μM of DOP-PCR 6MW, 5U of Taq polymerase (Perkin Elmer, Norwalk, Conn., USA), and ultrapure water (Biotech International, Perth, WA, Australia) to a volume of 50 μl. These PCR tubes were placed into a MJ Research Minicycler (Boston, Mass., USA) for an initial denaturation step of 95° C. for 5 min. The subsequent cycling conditions contained 8 cycles of low stringent amplification of 94° C. for 1 min, 30° C. for 1.5 min, 72° C. for 3 min with a ramp of 1° C. per 4 seconds for increasing temperature from 30° C. to 72° C., and 26 cycles of high stringent amplification of 94° C. for 1 min. 62° C. for 1 min, 72° C. form 3 min with an addition of 14 seconds per cycle to the extension step. Finally an extension step of 72° C. for 10 min was added at the end of cycling amplification. PCR products were ready for seeding the second round DOP-PCR for labelling.

EXAMPLE 7

Second Round DOP-PCR for Cy3/Cy5 Labelling

5 μl of first round DOP-PCR products (1/10 vol) was transferred into fresh 0.5 ml PCR tubes and subjected to a second round DOP-PCR amplification for labelling of Cy3-dUTP/Cy5-dUTP (PA 53022/PA 55022, Amersham Phamacla Biotech, USA). Amplification was carried out in a volume of 50 μl for 25 cycles using a MJ Research Mimicycler (Boston, Wash., USA), and the similar cycling conditions were applied as labelling DNA libraries for FISH (described above) with an exception of replacing SpectrumRed or SpectrumGreen with either Cy3-dUTP or Cy5-dUTP. Either Cy3-dUTP or Cy5-dUTP was used at a concentration of 0.04 mM. PCR products were then purified by Ultraclean™ PCR clean-up kits (#12500-250, Mo Bio Laboratories, Inc., CA, USA), and eluted in 50 μl of either 10 mM Tris-HCl or H$_2$O. 5 μl of purified PCR products was electrophoresed on 1% agarose gels in 0.5×TBE (Tris, borate, EDTA) prestained with ethidium bromide and photographed. The remaining could be either immediately used in microarray/CGH experiments or stored at −20° C. for a short period of a few weeks.

EXAMPLE 8

Microarray/CGH Analysis

Equal amounts (5~10 μl) of Cy3-labeled test and Cy5-labelled reference single-cell DOP-PCR products were mixed with 70 μg of human Cot-1 DNA (GIBICO, BRL) and 20 μg of Salmon sperm DNA (GIBICO, BRL). The resultant DNA mixture was precipitated with ethanol and resuspended in 10 μl of hybridization solution containing 50% deionized formamide, 2×SSC, 0.1% SDS, 10% dextran sulfate, and 5× Denhardt's solution. The hybridization mixture was heated to 80° C. for 10 min to denature DNA probes followed by preannealing of repetitive sequences at 37° C. for 180 min. Hybridization was carried out at 37° C. for 17~20 hrs. Post-hybridization washing included three times of 50% formamide/2×SSC, pH 7.0 at 45° C. for 10 min, twice of 2×SSC at 45° C. for 5 min ,and once of 1×SSC at room temperature for 10 min. Finally, slides were briefly rinsed in H$_2$O for a few seconds and dried by air in the dark, and then scanned as soon as possible.

EXAMPLE 9

Slides Scanning and Data Analysis

Microarray slides were scanned by a dual laser scanner called GenePix 4000B (Axon Instruments, Inc., CA, USA), which is capable of scanning Cy3 (at 532 nm) and Cy5 (at 635 nm) simultaneously and produces a ratio image in real time. These images were further analysed by a software of GenePix Pro 3.0.6.66 (Axon Instruments, Inc. USA). This software calculated both signal and local background intensities at both wavelengths (Cy3/Cy5) for all DNA dots and produced numerous raw data, among which five different ratios of Ratio of Medians, Ratio of Means, Median of Ratios, Mean of Ratio and Regression Ratio were most important. This software also presented a normalization factor for each of the five ratios by using global normalization on the assumption that the mean value of all the analysed features is 1.0. The normalized ratios could be either combined or compared across different array experiments. Ratios of Medians were selected in this study, and the averages of normalized ratios (Cy5/Cy3) from all suitable dots of the same probes were finally used for final analyses. A normalized ratio value of 1.0 was considered that there was no difference of copy numbers between the test and reference. Large changes in ratios indicated significant differences of copy numbers. A cut off threshold of less than 0.80 (autosomal) or 0.75 (sex chromosome) for trisomies and greater than 1.2 (autosomal) or 1.25 (sex chromosome) for monosomies was used in this study to determine aneuploidies of single copy changes. These criteria of threshold cutoffs is frequently used in comparative genomic hybridization for diagnosing single copy changes of genomic sequences.

The definition of Ratio of Medians was the ratio of the median intensities of each feature (DNA dot) for each Wavelength, with the median background subtracted. The steps used to determine the Normalization Factor for the Ratio of Medians by the software were as follows:

1) The Log value for each feature's Ratios of Medians Value is determined
2) The Average of all of the Log values is calculated ("Avglog")
3) The True average is calculated ("TrueAvg"). TrueAvg=10^Avglog
4) The Normalization Factor (NP) is determined. NF=1/TrueAvg
5) The Normalizated Ratios of Medians were calculated by NF X Ratios of Medians

EXAMPLE 10

Results of Single-Cell DNA Microarray/CGH

Single amniocytes of 47, XX, +13 and 47, XY, +18 were used as test samples and labelled with Cy3-dUTP (green), whereas single lymphocytes from a normal male 48, XY was used as a reference sample and labelled by Cy5-dUTP (red). After post-hybridization washing, array slides were dried and scanned immediately by GenePix 4000B, which could produced both single-wavelength and double-wavelength. images, These images could be saved in 24-bit JPEG images and by default as 16-bit unsigned TIFF images. The entire CGH procedure took approximately 30 hours.

Figure 5:
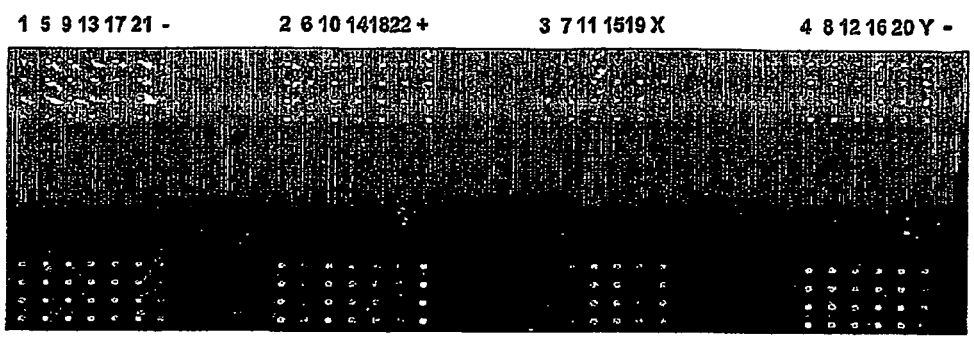
FIG. 5 shows the image and graphical representation of the data for the analysis of 47, XX, +13(Green) cell versus a 46, XY(Red) cell as described in Example 10.
Figure 5:
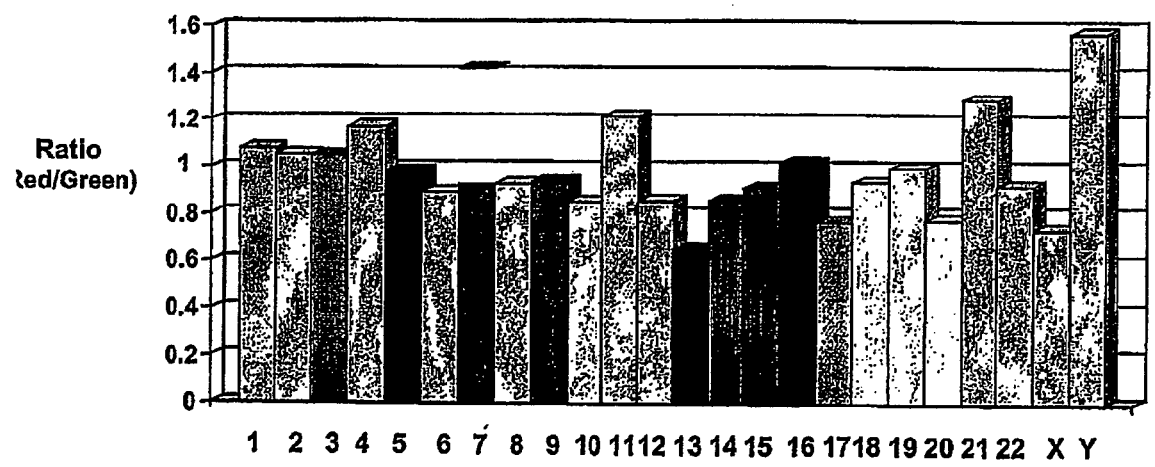

FIG. 5 was obtained from single-cell microarray/CGH experiments of 47, XX, +13 versus 46, XY. Preliminary analysis showed several chromosomal regions that appeared greener or redder on the target DNA dots. However, the final interpretation of copy numbers for target chromosomes was obtained from ratios of their corresponding DNA dots (see graphs).

Figure 6:
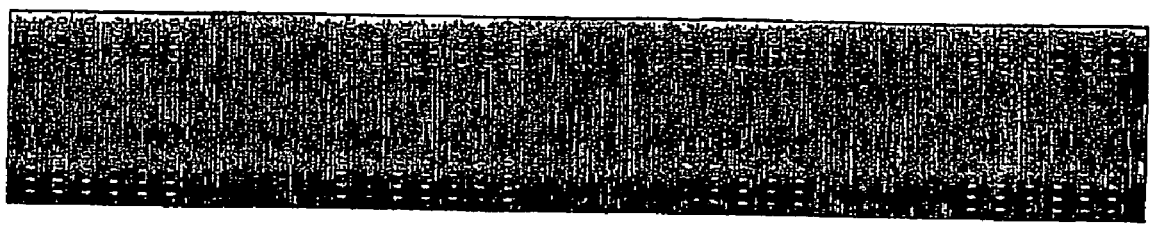
FIG. 6 shows the image and graphical representation of the data for the analysis of a 47, XY, +18 cell versus a 46, XX cell as described in Example 10.
Figure 6:
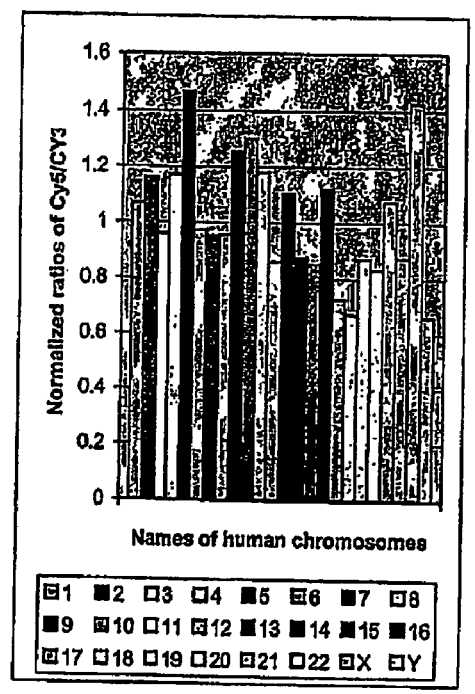

Similarly, FIG. 6 was obtained from single-cell microarray/CGH experiments of 47, XY, +18 versus 46, XY. The graph gives the final interpretation of copy numbers for target chromosomes obtained from ratios of their corresponding DNA dots.

16-bit unsigned TIFF images are standard uncompressed graphic file formats that can be read by many graphics and imaging programs. These images were used for extraction of data. The TIFF images were analysed in this study by GenePix Pro 3.0.6.66, which produced comprehensive data report sheet (in Excel format) for every microarray/CGH experiments. Ratios of Medians were selected in this study to interpret the final results, and in this study averaged ratios of medians from all suitable DNA dots of same DNA probes were finally used. Averaged ratios of medians of all human chromosomes for the images of FIGS. 5 and 6 are given in Table 1.

TABLE 1

| Name of Chromosome | Averages of ratios 47, XX, +13 v 46, XY (Cy3/Cy5) | Averages of ratios 47, XY, +18 v 46, XY (Cy3/Cy5) |
|---|---|---|
| No. 1 | 1.076990539 | 1.067886663 |
| No. 2 | 1.05202167 | 1.162437071 |
| No. 3 | 1.048407129 | 0.962005996 |

TABLE 1-continued

| Name of Chromosome | Averages of ratios 47, XX, +13 v 46, XY (Cy3/Cy5) | Averages of ratios 47, XY, +18 v 46, XY (Cy3/Cy5) |
|---|---|---|
| No. 4 | 1.172823435 | 1.171398634 |
| No. 5 | 0.980301567 | 1.466064292 |
| No. 6 | 0.888891728 | 0.971954515 |
| No. 7 | 0.92265915 | 0.95221539 |
| No. 8 | 0.926083452 | 0.957544954 |
| No. 9 | 0.933597893 | 1.25382922 |
| No. 10 | 0.846801349 | 1.29962399 |
| No. 11 | 1.213487021 | 1.180399675 |
| No. 12 | 0.853697513 | 0.859994198 |
| No. 13 | 0.647050399 | 1.10381187 |
| No. 14 | 0.853412154 | 0.876101324 |
| No. 15 | 0.908581464 | 0.850519418 |
| No. 16 | 1.015400663 | 1.12276143 |
| No. 17 | 0.765236378 | 0.723399453 |
| No. 18 | 0.9321711 | 0.669077381 |
| No. 19 | 0.991382989 | 0.871995586 |
| No. 20 | 0.773321535 | 0.831411945 |
| No. 21 | 1.28601564 | 1.074005791 |
| No. 22 | 0.917237339 | 0.872627238 |
| X | 0.732895748 | 1.425362216 |
| Y | 1.568758354 | 0.66007634 |

A graphical representation of the results in Table 1 is in FIG. 6.

The data in Table 1 show that in the single-cell microarray/CGH experiments averaged ratios of medians for dots of 13, 18, X, and Y were 0.6470, 0.9321, 0.7328, and 1.568, respectively for 47, XX, +13 versus 46, XY.

In the case of 47, XY, +18 versus 46, XX, these ratios were shifted to 1.1038, 0.6691, 1.4254, and 0.6601 for chromosomes 13, 18, X and Y, respectively. If out-off threshold of 0.75-1.25 applied to determine single-copy changes of chromosomes, trisomies 13 and 18 plus the differences of copy numbers of chromosome X and Y could be correctly established for all testing and reference samples used in these two single-cell microarray/CGH experiments.

The expected averaged ratios of medians for all other 20 different chromosomes should be within the cut-off threshold of 0.75-1.25, as there were no any differences of copy numbers for these chromosomes between the test and reference samples. The data in Table 1 demonstrate that the majority of the other 20 chromosomes fit quite well within this threshold. Averaged ratios of medians were found to be 1.2860 for chromosome 21 for 47, XX, +13 versus 46, XY, and 1.47660, 1.2996, and 0.72339 for chromosomes 5, 10 and 18 for 47, XY, +18 versus 46, XX.

EXAMPLE 11

Reproducibility of CGH Performed with DNA Array with Size Selected PCR Amplified DNA (Second Generation Array).

Experimental protocols were the same as described above with the exception that the second generation array with size selected DNAs was used. This array also contains the original DNA libraries prior to size selection. Aliquots of normal male and normal female cell DOP-PCR reactions were labelled with either Cy3 or Cy5 and hybridised as per the combinations described in Table 2 below.

TABLE 2

| Slides | Microarray/CGH experiments | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| NH1 rh | $DH_1Cy_3/NH_9Cy_5$ |  | # |  |  |  |  |  |  | # | # |  |  |  |  |
| NH3 rh | $DH_{29}Cy_3/NH_{44}Cy_5$ |  |  |  | # |  |  |  |  |  |  |  |  |  |  |
| NH6 lh | $DH_1Cy_3/NH_9Cy_5$ |  |  |  |  |  |  |  |  |  |  |  |  |  |  |
| NH6 rh | $DH_7Cy_5/NH_{15}Cy_3$ |  |  |  |  |  |  |  | # |  |  |  |  |  |  |
| NH7 lh | $DH_1Cy_5/NH_{21}Cy_3$ |  |  |  |  |  |  |  |  |  |  |  |  |  |  |
| NH7 rh | $DH_{13}Cy_5/NH_{27}Cy_3$ |  |  |  |  |  |  |  |  |  |  |  |  |  |  |
| NH8 lh | $DH_{31}Cy_5/NH_{31}Cy_3$ |  |  |  |  |  |  |  |  |  |  |  |  |  |  |
| NH8 rh | $DH_{45}Cy_5/NH_{37}Cy_3$ |  |  |  |  |  |  |  |  |  |  |  | # |  |  |
| NH9 lh | $DH_1Cy_5/DH_1Cy_3$ |  |  |  |  |  |  |  |  |  |  |  |  |  |  |
| NH10 lh | $DH_{17}Cy_5/NH_{32}Cy_3$ |  |  |  |  |  |  |  |  |  |  |  |  |  |  |
| NH10 rh | $DH_{13}Cy_5/NH_{43}Cy_3$ |  |  |  |  |  |  |  |  |  |  |  |  |  |  |
| NH11 rh | $DH_{23}Cy_5/NH_{36}Cy_3$ |  |  |  |  |  |  |  |  |  |  |  |  |  |  |
| NH12 lh | $NH_9Cy5/NH_9Cy3$ |  |  |  |  |  |  |  |  |  |  |  |  |  |  |
| Nh12 rh | $DH_{37}Cy_5/NH_{50}Cy_3$ |  |  |  | # | # |  |  |  |  |  | # |  |  |  |
| Total Expected ratios | 14 separate microarray/CGH experiments | 14 | 13 | 14 | 12 | 13 | 14 | 14 | 13 | 13 | 13 | 12 | 14 | 14 | 14 |

| Slides | Microarray/CGH experiments | 15 | 16 | 17 | 18 | 19 | 20 | 21 | 22 | X | Y (37) | Y (26) |
|---|---|---|---|---|---|---|---|---|---|---|---|---|
| NH1 rh | $DH_1Cy_3/NH_9Cy_5$ |  |  |  |  |  |  |  |  | # | # |  |
| NH3 rh | $DH_{29}Cy_3/NH_{44}Cy_5$ |  |  |  |  |  |  |  |  | # |  |  |
| NH6 lh | $DH_1Cy_3/NH_9Cy_5$ |  |  |  |  |  |  |  |  |  |  |  |
| NH6 rh | $DH_7Cy_5/NH_{15}Cy_3$ |  |  |  |  |  |  |  | # |  |  | # |
| NH7 lh | $DH_1Cy_5/NH_{21}Cy_3$ |  |  |  |  |  |  |  |  |  |  | # |
| NH7 rh | $DH_{13}Cy_5/NH_{27}Cy_3$ |  |  |  |  |  |  |  |  |  |  | # |
| NH8 lh | $DH_{31}Cy_5/NH_{31}Cy_3$ |  | # |  |  |  | # |  | # |  |  | # |
| NH8 rh | $DH_{45}Cy_5/NH_{37}Cy_3$ |  |  |  |  |  |  |  |  |  |  |  |
| NH9 lh | $DH_1Cy_5/DH_1Cy_3$ |  |  |  |  |  |  |  |  |  |  | # |
| NH10 lh | $DH_{17}Cy_5/NH_{32}Cy_3$ |  |  |  |  |  |  |  |  |  | # | # |
| NH10 rh | $DH_{13}Cy_5/NH_{43}Cy_3$ |  |  |  |  |  |  |  |  | # | # | # |
| NH11 rh | $DH_{23}Cy_5/NH_{36}Cy_3$ |  |  |  |  |  |  |  |  |  |  |  |
| NH12 lh | $NH_9Cy5/NH_9Cy3$ |  |  |  |  |  |  |  |  |  |  |  |
| Nh12 rh | $DH_{37}Cy_5/NH_{50}Cy_3$ |  |  |  |  |  |  |  |  |  | # | # |
| Total Expected ratios | 14 separate microarray/CGH experiments | 14 | 14 | 13 | 14 | 14 | 13 | 14 | 12 | 13 | 9 | 5 |

(1) Total single lymphocytes used here including 10 DH cells and 11 NH cells
(2) Cells used more than once including DH1, NH9, DH13

Figure 7:
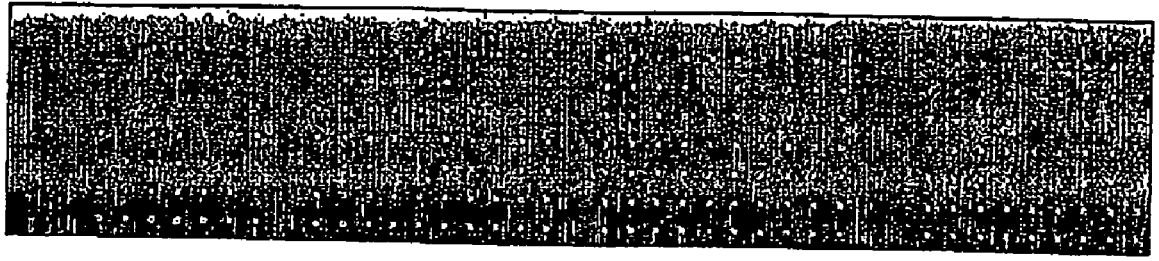
FIG. 7 shows one of the images which is representative of the experiments described in Example 11.

Table 2 shows that single cell comparative genomic hybridization experiments using our array are extremely reproducible with all chromosomes (except the Y chromosome) producing perfect results in at least 13 of the 14 experiments. The size selected Y chromosome spots were more accurate than the non-size selected ones. The data corresponding to one of the above experiments (NH7 lh) is shown in FIG. 7. Table 3 shows the ratios calculated by the computer:

TABLE 3

| | NH7 lh - Normalization of Median of ratios | | | | Log2 value of |
|---|---|---|---|---|---|
| | Raw Median of ratios | Log Value | NF | Normalization Median of Ratios | normalized median of ratios |
| 1 | 0.575125 | −0.240238 | 1.826851 | 1.050667624 | 0.071306348 |
| 2 | 0.463125 | −0.334302 | 1.826851 | 0.846060323 | −0.241167565 |
| 3 | 0.619875 | −0.207696 | 1.826851 | 1.132419202 | 0.179408117 |
| 4 | 0.53225 | −0.273884 | 1.826851 | 0.972341392 | −0.040465158 |
| 5 | 0.49625 | −0.304299 | 1.826851 | 0.906574759 | −0.141502101 |
| 6 | 0.592625 | −0.22722 | 1.826851 | 1.082637515 | 0.114550285 |
| 7 | 0.60325 | −0.219503 | 1.826851 | 1.102047805 | 0.140186808 |
| 8 | 0.502125 | −0.299188 | 1.826851 | 0.917307508 | −0.124522647 |
| 9 | 0.459125 | −0.338069 | 1.826851 | 0.838752919 | −0.253682212 |
| 10 | 0.501375 | −0.299837 | 1.826851 | 0.91593737 | −0.126679142 |
| 11 | 0.642125 | −0.19238 | 1.826851 | 1.173066634 | 0.230284966 |
| 12 | 0.55375 | −0.256686 | 1.826851 | 1.011618686 | 0.016665591 |
| 13 | 0.548875 | −0.260527 | 1.826851 | 1.002712788 | 0.003908426 |
| 14 | 0.558875 | −0.252685 | 1.826851 | 1.020981297 | 0.029956438 |
| 15 | 0.543875 | −0.264501 | 1.826851 | 0.993578533 | −0.009294091 |
| 16 | 0.619625 | −0.207871 | 1.826851 | 1.131962489 | 0.178826151 |
| 17 | 0.58675 | −0.231547 | 1.826851 | 1.071904766 | 0.100176734 |
| 18 | 0.543125 | −0.2651 | 1.826851 | 0.992208395 | −0.011284931 |
| 19 | 0.5925 | −0.227312 | 1.826851 | 1.082409158 | 0.114245951 |
| 20 | 0.5265 | −0.278602 | 1.826851 | 0.961836999 | −0.056135672 |
| 21 | 0.46775 | −0.329986 | 1.826851 | 0.854509508 | −0.226831549 |
| 22 | 0.5675 | −0.246034 | 1.826851 | 1.036737886 | 0.052051189 |
| X | 0.412375 | | 1.826851 | 0.75334764 | −0.40861233 |
| Y | 0.49825 | | 1.826851 | 0.910228461 | −0.135699398 |

EXAMPLE 12

Single Cell CGH Using DNA Array with Size Selected PCR Amplified DNA Libraries (Second Generation Array) for the Detection of Trisomy 18 and Gender.

Figure 8:
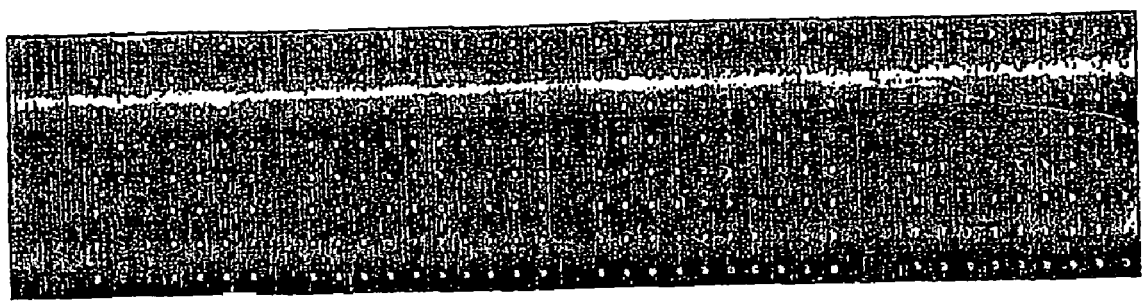
FIG. 8 shows the image for the experiment of the analysis of a single cell with karyotype 47, XY, +18 versus a 46, XX single cell as described in Example 12.
Figure 9:
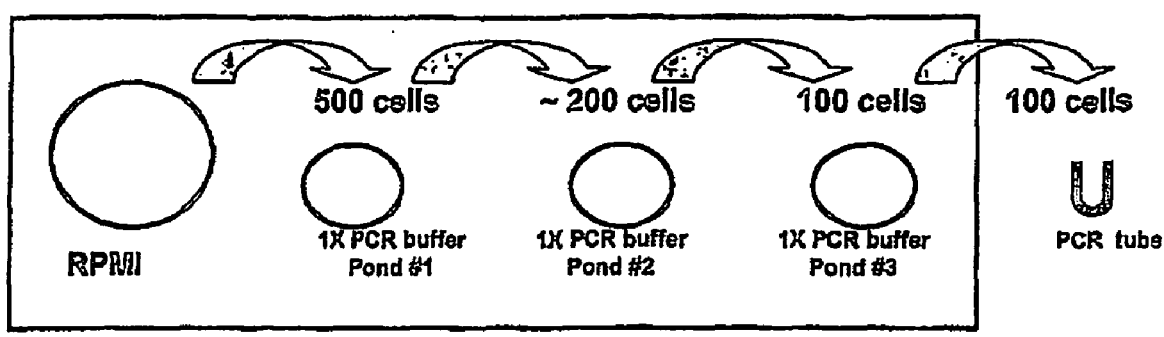
FIG. 9 shows the procedures of isolation of fibroblast cells. A fibroblast cell suspension is diluted through four ponds created on a microscope slide up to the point where there are only around 100 cells in the 1×PCR buffer pond #3. These 100 hundred cells were washed for several times in this pond and then transferred into a 0.5 ml sterilized PCR tube. 1×PCR buffer (<3 µl) was aspirated from the pond #3 and used for a negative control.

Single amniocytes of 47, XY, +18 were used as the test sample against single a single lymphocte 46, XX using the second generation array as described previously. FIG. 8 shows the results of the hybridization to the array. The raw data and normalised ratios are shown in Table 4. As can be seen, the presence of trisomy 18 was successfully detected.

TABLE 4

| NH25 lh - Normalization of Median of ratios | | | Normalization | Log2 value of |
|---|---|---|---|---|
| Raw Median of ratios | Log Value | NF | Median of Ratios | normalized median of ratios |
| 1 | 0.646375 | −0.189515449 | 1.6053857 | 1.037681182 | 0.053363257 |
| 2 | 0.592875 | −0.227036862 | 1.6053857 | 0.951793047 | −0.07128018 |
| 3 | 0.6595 | −0.1807852 | 1.6053857 | 1.058751869 | 0.082364517 |
| 4 | 0.603879 | −0.219050073 | 1.6053857 | 0.969458711 | −0.044748639 |
| 5 | 0.592625 | −0.227220032 | 1.6053857 | 0.9513917 | −0.071888655 |
| 6 | 0.6905 | −0.160836317 | 1.6053857 | 1.108518826 | 0.148633272 |
| 7 | 0.7086667 | −0.149557974 | 1.6053857 | 1.137683386 | 0.186099116 |
| 8 | 0.629 | −0.201349355 | 1.6053857 | 1.009787605 | 0.014051874 |
| 9 | 0.58425 | −0.233401279 | 1.6053857 | 0.937946595 | −0.092422314 |
| 10 | 0.646625 | −0.189347509 | 1.6053857 | 1.038082528 | 0.053921143 |
| 11 | 0.62125 | −0.206733598 | 1.6053857 | 0.997345866 | −0.003834196 |
| 12 | 0.62325 | −0.205337713 | 1.6053857 | 1.000556638 | 0.000802835 |
| 13 | 0.62875 | −0.201522002 | 1.6053857 | 1.009386259 | 0.013478352 |
| 14 | 0.63014286 | −0.20056098 | 1.6053857 | 1.011622336 | 0.016670797 |
| 15 | 0.59485714 | −0.225587321 | 1.6053857 | 0.954975146 | −0.066464908 |
| 16 | 0.656 | −0.183096161 | 1.6053857 | 1.053133019 | 0.074687672 |
| 17 | 0.67825 | −0.168610198 | 1.6053857 | 1.088852851 | 0.122809 |
| 18 | 0.48228571 | −0.316695606 | 1.6053857 | 0.774254582 | −0.369120079 |
| 19 | 0.5755 | −0.239954672 | 1.6053857 | 0.92389947 | −0.114192215 |
| 20 | 0.663 | −0.178486472 | 1.6053857 | 1.064370719 | 0.090000727 |
| 21 | 0.5695 | −0.244506272 | 1.6053857 | 0.914267156 | −0.129312301 |
| 22 | 0.67057143 | −0.173554954 | 1.6053857 | 1.076525785 | 0.106382875 |
| X | 0.69885714 | | 1.6053857 | 1.121935259 | 0.165989428 |
| Y | 0.69525 | | 1.6053857 | 1.116144408 | 0.158523697 |

EXAMPLE 13

Array CGH Using a Sample of Around 100 Cells
(i) Preparation of Samples

Two tubes containing a fibroblast cell line (47, XY, +18) were thawed from liquid nitrogen and incubated immediately at 37° C. for 10 min, washed using 1×PBS twice, and then resuspended in 500 μl of 1×PBS.

Figure 10:
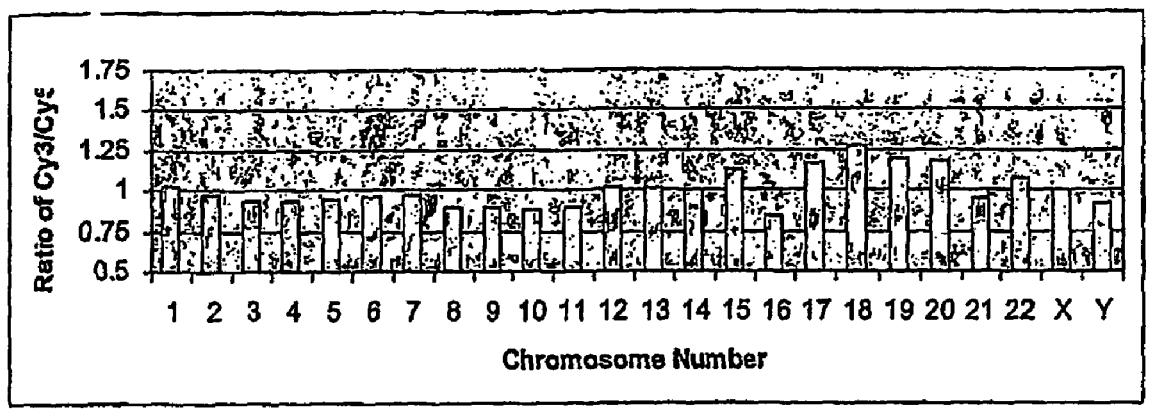
FIG. 10 in the top panel shows the results of an array CGH experiment of 100 fibroblast cells (47, XY, +18, Cy3) versus a normal male genomic DNA (46, XY, Cy5).
Figure 10:
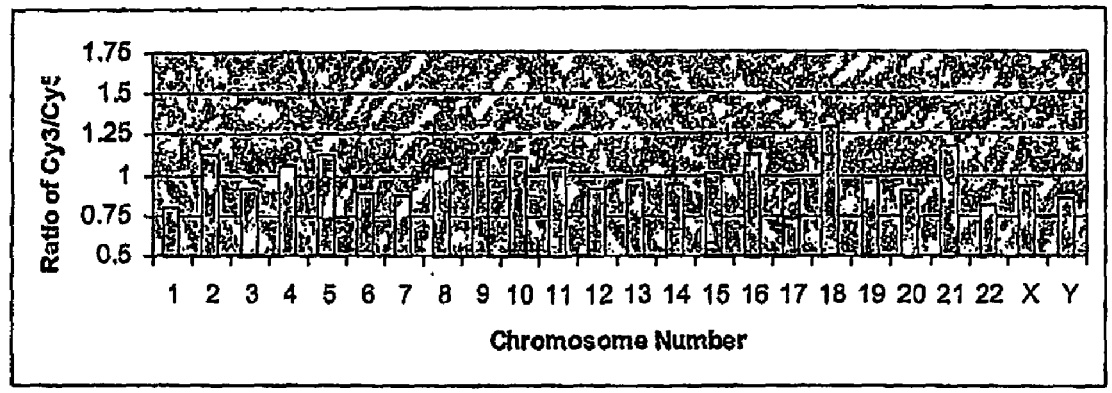

Cell sorting was performed as shown in FIG. 10 on a superfrost microscope glass slide (Menzel-Glaser, Germany) using an inverted light microscope under a 20×10 magnification (CK2, Olympus, Japan). Briefly, slides were washed thoroughly with sterilized 70% ethanol (Delta West Pty Ltd, Australia) and mounted onto the microscope. 100 μl of RPMI medium (Sigma) was pipetted onto the left side of the slide and 1 μl of the fibroblast cell suspension was added. Another three smaller ponds (approximately 50 μl) of 1×PCR buffer (50 mM KCl, 10 mM Tris-HCl, pH 8.3) were created to the right of the RPMI pond in sequence and designated (from left to right) as 1×PCR buffer pond #1, pond #2, and pond #3, respectively (FIG. 10). Using a 9", extruded, cotton-plugged glass Pasteur pipette, fibroblast cells were aspirated from the RPMI pond and approximately five hundred cells were then transferred to the 1×PCR buffer pond #1. Using a fresh pipette, less than two hundred cells were transferred into the 1×PCR buffer pond #2. Around one hundred cells were aspirated with a fresh pipette from the pond #2 and transferred into the 1×PCR buffer pond #3. These cells were aspirated and gently pumped in and out the end of pipette at a fresh location with a fresh pipette. After washing, these cells were aspirated into the end of the pipette with a minimal amount of PCR buffer and then transferred into a 0.5 ml sterilized PCR tube. Isolated cells were used immediately (II) Array CGH Using a Sample of Around 100 Cells Samples of around 100 cells were labelled with Cy3-dUTP as described in Examples 6 and 7.

Two separate array CGH experiments (Experiment A and Experiment B) were carried out, as follows:

Experiment A

In this experiment array CGH was carried out using 100 fibroblast cells (48, XY, +18, Cy3) versus a normal male genomic DNA (46, XY, Cy5): the results of this experiment are shown in FIG. 10 (top panel). As expected, an expected ratio of >1.25 for chromosome 18 was obtained along with an expected ratio within the range 0.75-1.25 for all 21 other autosomes. The ratio of X chromosome obtained was also in the range of 0.75-1.25, indicating the correct determination of the gender of male for the test fibroblast cell line.

Experiment B

In this experiment array CGH was conducted using 100 fibroblast cells (48, XY, +18, Cy3) versus a pooled mixture (46, XY, Cy5) of 5 up to 10 single normal male cells. The results of this experiment are shown in FIG. 10 bottom panel. An expected ratio of >1.25 was obtained for chromosome 18 and the ratios of all 21 other autosomes were in the range 0.75-1.25. An ratio in the range 0.75-1.25 was also obtained for the X chromosome, indicating the correct diagnosis of the gender of male for the test fibroblast cell line.

EXAMPLE 14

Array CGH Using DOP-PCR Amplified Cot-1 DNA
(i) Amplification of Cot-1 DNA 100 ng of Cot-1 DNA (Cat. No., 15279-011, Invitrogen) was amplified using DOP-PCR in a Minicycler (MJ Research, USA) in a volume of 50 μl containing 5 U of Taq polymerase (Applied Biosystems), and a final concentration of 50 mM KCl, 10 mM Tris-HCl pH 8.3, 0.1 mg/ml gelatin, 2.5 mM MgCl$_2$, 200 μM of each dNTP, 2 μM DOP-PCR 6MW primer (5' CGACTCGAGNNNNNNATGTGG-3'-SEQ ID NO.1) (Telenius et al. 1992). The sample was centrifuged briefly, denatured at 95° C. for 5 min, and cycled for 8 cycles of: 94° C. for 1 min, 30° C. for 1.5 min, 72° C. for 3 min with a ramp of 1° C. per 4 seconds between the annealing and the extension steps, followed by 29 cycles of 94° C. for 1 min, 62° C. for 1 min, 72° C. for 3 min initially, but increased by 14 seconds for each cycle, and a final extension step at 72° C. for 10 min. 5 μl of amplified products was run on a 1% Agarose gel (FIG. 11 top panel) and the rest purified.

As shown in lane 1, the amplified Cot-1 DNA was a smear with the majority ranging from 250 bp to 2 kb. DNA markers were SPP-1/EcoRI ($M_1$) and pUC19/HpaII ($M_2$).

(ii) Results of Array CGH Using DOP-PCR Amplified Cot-1 DNA

Figure 11:
FIG. 11 in the top panel shows agarose electrophoresis of DOP-PCR-amplified Cot-1 DNA FIG. 11 in the bottom panel shows the results of an array CGH experiment of a single female cell labelled with Cy3-dUTP versus a pooled mixture of more than 5 single male cells labelled with Cy5-dUTP using 140 μl of DOP-PCR amplified Cot-1 DNA instead of 70 μg of commercialized Cot-1 DNA (Invitrogen).
Figure 11:
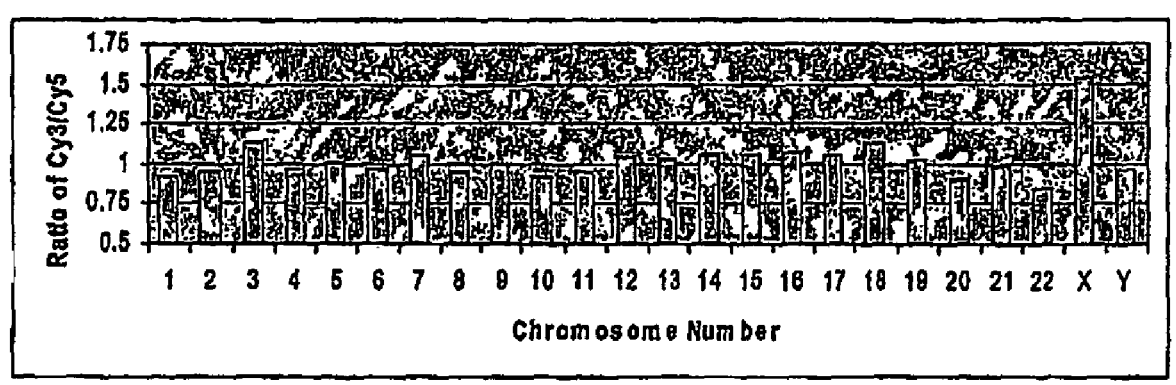

One array CGH experiment of a single female cell labelled with Cy3-dUTP versus a pooled mixture of 5 single male cells labelled with Cy5-dUTP was carried out exactly as described previously, except that 140 μl of DOP-PCR-amplified Cot-1 DNA was used instead of 70 μg of Cot-1 DNA (Cat. No., 15279-011, Invitrogen). The ratios of all 24 chromosomes obtained from this experiment are shown in FIG. 11 bottom panel, which indicates that the ratios of all 22 autosomes are within the range of 0.75-1.25 and an expected ratio of >1.25 for X chromosome was obtained. However, the result for the Y chromosome was inadmissible.

As expected, all the ratios of 22 autosomes are within the range of 0.75-1.25, and the X chromosome gives a ratio of >1.25, correctly indicating the gender of female for the test single cell.

EXAMPLE 15

Blastomere Array CGH Analyses
1. Material and Methods
(i) Preparation of Single Blastomeres Three frozen human IVF embryos used were obtained from IVF Australia, Westmead, NSW, Australia: where the embryos were thawed, briefly incubated, disaggregated, and each cell was aspirated into a polymerase chain reaction (PCR) tube. These PCR tubes were placed in dry ice and posted to our laboratory by express mail. A total of 12 single blastomeres were obtained from the three frozen embryos.

(ii) Lysis of Single Blastomeres

Lysis of single blastomeres was carded out using 5 μl of lysis buffer (200 mM KOH, 50 mM dithiothreitol) at 65° C. for 10 min followed by neutralization using 5 μl of neutralisation solution (300 mM KCl, 900 mM Tris-HCl, 200 mM HCl, pH 8.3).

(iii) First round of DOP-PCR for random amplification of single cells First round of DOP-PCR was performed in a Minicycler (MJ Resrearch, USA) in a volume of 50 μl containing the single-cell lysed and neutralized solution (10 μl), 5 U of Taq polymerase (Applied Biosystems), and a final concentration of 50 mM KCl, 100 mM Tris-HCl pH 8.3, 0.1 mg/ml gelatin, 2.5 mM $MgCl_2$, 200 μM of each dNTP, 2 M DOP-PCR 6MW primer (5'-CCGACTCGAGNNNNNNAT-GTGG-3'-SEQ ID NO.1) (Telenius et al. 1992). The sample was centrifuged briefly, denatured at 95° C. for 5 min, and cycled for 8 cycles of: 94° C. for 1 min, 30° C. for 1.5 min, 72° C. for 3 min with a ramp of 1° C. per 4 seconds between the annealing and the extension steps, followed by 26 cycles of 94° C. for 1 min, 62° C. for 1 min, 72° C. for 3 min initially, but increased by 14 seconds for each cycle, and a final extension step at 72° C. for 10 min.

(iv) Second Round of DOP-PCR for Cy3/Cy5 Labelling

First round of DOP-PCR products (5 μl) were labelled in a volume of 50 μl, containing 5 U of Taq polymerase (Applied Biosystems), and a final concentration of 50 mM KCl, 10 mM Tris-HCl pH 8.3, 2.5 mM $MgCl_2$, 160 μM for each of dGTP, dCTP, and dATP, 120 μM dTTP, 40 μM of either Cy3-dUTP or Cy5-dUTP (Amersham Phamacia Blotech, USA), and 2 μM DOP-PCR 6MW primer. The sample was centrifuged briefly, denatured at 95° C. for 4 min, and cycled for 25 cycles of: 94° C. for 1 min, 62° C. for 1 min, 72° C. for 3 min initially but increased by 10 seconds for each cycle. An extension step at 72° C. for 10 min was added at the end. Normally, 5 μl of each DOP-PCR product was run on 1% agarose gels in 0.5× TBE to check the quality of amplification and the remaining products were purified.

(v) Purification of Cy3- and Cy5-Labelled Products

Cy3- or Cy5-labelled DOP-PCR products were purified by UltraClean™ PCR Clean-up kit (Mo Bio Laboratories, USA) according to the manufacturer's instructions. Briefly, 5 volumes of SpinBind (Guanidine HCl/isopropanol) was added to the PCR products (45 μl) and then mixed thoroughly by pipetting. The PCR/SpinBind mixture was transferred to a spin filter unit and centrifuged at 14,000 rpm in a microcentrifuge for 10-30 seconds. The liquid flow in the collection tube was discarded and 300 μl SpinClean buffer (ethanol solution) was then added to the same spin filter unit followed by centrifuging at 14,000 rpm for 30-60 seconds. The collection tube containing the liquid flow was replaced with a fresh collection tube and 50 μl of Elution buffer (10 mM Tris, pH 8.0, DNase-free) was directly added onto the filter membrane of the same spin. filter unit followed by centrifuging 30-60 seconds at 14,000 rpm. The spin filter basket was discarded and the collection tube contained the purified Cy3- or Cy5-labeled probes. These purified probes were free of all PCR reaction components such as DOP-PCR 6MW primer, salt, Taq polymerase, and Cy3- and Cy5-dUTP and used immediately in array CGH or stored at –20° C. at least for two months prior to array CGH analysis. 5 ul of each purified product was always run on a 1% agarose gel to check the efficiency of both labelling and purification.

(vi) Array CGH

Equal volumes (5~10 μl) of each of Cy3-labeled (test) and Cy5-labelled (reference) DOP-PCR products were mixed with 70 μg of human Cot-1 DNA (GIBCO, BRL), 20 μg of sheared salmon sperm DNA (GIBCO, BRL) and precipitated with two volumes of 100% ethanol, and 1/10 volume of 3 M NaAC (pH 5.2). The resulting mixture was placed at –20° C. for 2 hours and then centrifuged at 14,000 rpm for 25 min at 4° C. The resultant DNA pellets were washed once with 70% ethanol followed by centrifuging at 14,000 rpm for 10 min at 4° C., dried either by air in the dark or at 60° C. in an oven, and finally dissolved in 10 μl of hybridization solution (50% deionized formamide, 3×SSC, 0.1% SDS, 10% dextran sulfate, and 5×Denhardt's solution). After denaturation at 80° C. for 10 min and preannealing at 37° C. for 80 min, the probe mixture was applied to the array area and covered with a coverslip. Hybridization was carried out at 37° C. for 15~20 hours in a humid incubator. After hybridization, the slides were immersed in 50% formamide/2×SSC until the coverslips fell off by themselves (normally taking 10 min). Post-hybridization washing included twice in 50% formamide/2× SSC at 45° C. for 10 min, twice in 2×SSC at 45° C. for 5 min, once in 1×SSC at room temperature for 10 min, and three times of a brief rinse in MilliQ $H_2O$. All of the above solutions used in washing were filtered through a 0.22 μm filter (MILLIPORE, USA) prior to washing. After washing, the slides were dried in the dark and then scanned immediately, or they could be stored in the dark at room temperature for at least 73 days.

(vii) Array Scanning and Data Analysis

GenePix 4000B is an integrated scientific instrument with a GenePix 4000B scanner for scanning slides and the software GenePix Pro for data analysis (Axon Instruments, Union City, Calif., USA). GenePix 4000B lasers excite at 532 nm (green) and 636 nm (red). The emission filters are 575DF35 (green; ~557-592 nm) and 670DF40 (red; ~650-690 nm). These lasers and filters are optimized for Cy3 and Cy5. GenePix 4000B scanner scans Cy3 and Cy5 simultaneously and it takes about 5 minutes for a full scan of a standard microscope slide (25 mm×75 mm) at a resolution of 10 microns (and under 12 minutes for a full scan at 5 microns resolution), and much less time for user-defined sub-scans.

Array Scanning:

Briefly, a Preview Scan (40 micron resolution) was used to locate the array on the slide and set the scanning parameters including Photomultiplier tube (PMT) voltages, scan area, and laser powers. A high-resolution (10 micron) Data Scan was then used to acquire the images for CGH analysis. Photomultiplier tube (PMT) gains (voltages) of both channels used in this study ranged from 400 to 900 whereas laser powers of both channels were always at 100% level. The primary data acquired by GenePix 4000B are the single-wavelength images, and by default these were saved as 16-bit grayscale TIFFs (Tagged Image File Format) in a single multi-image, which included the Cy5/Cy3 ratio image saved in both TIFF and JPEG (Joint Photographic Experts Group) format. TIFF files were used for analysis and JPEG files only for presentations.

Data Analysis:

Software of GenePix Pro 4.0.1.12 was used for analysis of the TIFF images. Briefly, GenePix Pro used a GenePix Array List files (GAL file) to locate the size and position of all features. After analysis, the results were saved as GPR files (GenePix Results format), which included a header consisting of general information about image acquisition and analysis as well as the data extracted from each feature including more than 40 different parameters. In this study, the median of pixel-by-pixel ratios (Cy3/Cy5) of pixel intensities with the median background subtracted was selected for interpretation.

Exclusion of Dots for Analysis:

Seven different parameters of the GPR files were used in this study for data filtering, including:
1. Dia.: the diameter in Em of the feature-indicator
2. >% B635+2 SD: the percentage of feature pixels with intensities more than two standard deviations above the background pixel intensity, at wavelength #1 (635 nm, for Cy5)
3. >% B532+2 SD: the percentage of feature pixels with intensities more than two standard deviations above the background pixel intensity, at wavelength #2 (523 nm, for Cy3)
4. SNR635: the signal-to-noise ratio at wavelength #1 (635 nm, for Cy6), defined by (Mean Foreground 1−Mean Background 1)/(Standard deviation of Background 1)
5. SNR532: the signal-to-noise ratio at wavelength #2 (532 nm, for Cy3), defined by (Mean Foreground 1−Mean Background 1)/(Standard deviation of Background 1)
6. F635% Sat.: the percentage of feature pixels at wavelength #1 (for Cy5) that are saturated
7. F532% Sat.: the percentage of feature pixels at wavelength #2 (for Cy3) that are saturated Dots were excluded from analysis if they failed to pass any of the following parameters of: (1) Dia. >50 μm, (2) >% B635+2 SD >70, (3) >% B532+2 SD >70, (4) SNR635>3.0, (5) SNR532>3.0, (6) F635% Sat.=0, and (7) F532% Sat.=0. The definitions of these parameters are as given by Axon Instruments.

Ratio Normalization

The mean of ratios for each chromosome was calculated from up to 8 qualified replicates. Normalization was then carried out using the 22 means of ratios from all autosomes assuming that the mean ratio value of all autosomes in each array CGH hybridization was 1.0. This normalization method was performed as described by the manufacturer (Axon Instruments) and can be briefly described as follows:

The median of ratios for all included dots was averaged for each chromosome to give the raw mean The Log value for each raw mean of median of ratios value is determined The Average of all of the Log values was calculated ("Avglog")

The True average was calculated ("TrueAvg"), TrueAvg=10^Avglog)

The Normalization Factor (NF) was determined (NF=1/TrueAvg)

the Normalization factor was applied to rescale all raw means of median of ratios (Normalized mean of median of ratios=NF times the raw mean of median of ratios) to give the normalised ratios.

Figure 12:
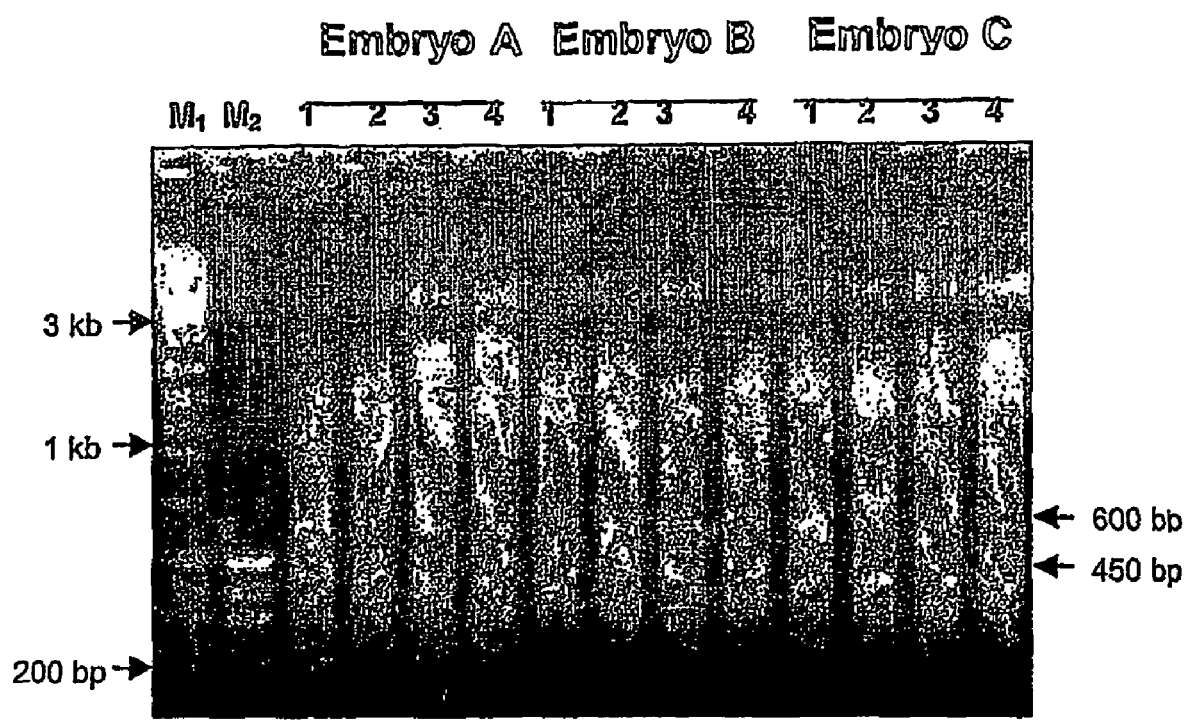
FIG. 12 shows agarose gel electrophoresis of Cy3-labelled DOP-PCR products generated from single blastomeres of IVF-created cleavage-stage embryos. Four blastomeres were present in each of three frozen embryos donated to research and all four blastomeres were dissociated resulting in a total of 12 separate single blastomeres. The DNA of each cell was preamplified and then labeled with Cy3 by DOP-PCR. The origin of each sample is indicated above each lane. DNA markers were SPP-1/EcoRI ($M_1$) and pUC19/HpaII ($M_2$). Note that each labelled product gives a smear on a 1% agarose gel ranging from 300 bp to 2,500 bp and containing two specific bands approximately at 450 bp and 600 bp.

2. Results of Blastomere Array CGH (i) Random Amplification and Labelling of Single Blastomeres by DOP-PCR After DOP-PCR preamplification and labelling with Cy3 as shown in FIG. 12, all of the 12 blastomeres, which were obtained from the three frozen IVF-created cleavage-stage embryos donated to research, produced a satisfactory Cy3-labelled product ranging from 300 bp to 2500 bp containing two specific bands, of approximately 450 bp and 600 bp, after being size fractionated on a 1% agarose gel stained with ethidium bromide.

(ii) Chromosomal Analyses of Single Blastomeres Using Array CGH

Array CGH analysis was performed using a pooled mixture of 5 to 10 normal male single-cell DOP-PCR products labelled with Cy5 as the reference material. Only 10 out of the 12 available blastomeres could be analysed because of limited availability of arrays. Of the 10 cells analysed using array CGH, 2 failed to produce analysable results due to a high fluorescence background, probably the result of the relative humidity adopted for the hybridization step accidentally being much lower than the standard 95%.

Of the 8 blastomeres producing analysable array CGH results, three were found to be normal with an apparently female karyotype (46, XX) (embryo A blastomeres 1 and 4, embryo C blastomere 2). Four cells were aneuploid, two of which had trisomy 21 and apparently female karyotypes (embryo A blastomere 2, embryo B blastomere 1). Two other cells were aneuploid for chromosome 21 (embryo B blastomere 2) and 18 (embryo C blastomere 3) with possible monosomies for chromosomes 1 and 12 respectively. Finally, one blastomere (embryo A blastomere 3) gave an apparently chaotic karyotype with a ratio of <0.75 for six different CSLs including $CSL_{1, 7, 8, 14, 17, \text{ and } 20}$, and a ratio of >1.25 for seven other CSLs containing $CSL_{2, 5, 10, 12, ,13, 18, \text{ and } 21}$. This result suggests that this blastomere had monosomy for six chromosomes, 1, 7, 8, 14, 17, and 20, and trisomy for seven other chromosomes, 2, 5, 10, 12, 13, 18, and 21.

All of the three embryos analysed were observed to be mosaic. Of the four cells analysed for embryo A, two were normal, one was trisomy 21, and the other had extensive aneuploidy (chaotic). Both cells analysed for embryo B had trisomy 21, and one of them had a possible monosomy 1. Of the two cells analysed for embryo C, one was normal and the other was trisomy 18 with a possible monosomy 12. Gender determination revealed that all three embryos had an apparently female karyotype and this was consistent for all cells from each embryo except the chaotic blastomere (embryo A blastomere 3) for which no weight can be given to the observed ratio of 0.90 for $CSL_x$ for the purposes of gender assignment.

EXAMPLE 16

Preparation of BAC DNA4 Probes for Array Printing
Source of BAC DNA probes (From Women Children's Hospital, Adelaide)

| | |
|---|---|
| RP-11-265k23 (5q35) | RP-11-849 (17p11.2) |
| RP-11-354m20 (10q25.2-26.11) | RP-11-280F22 (10q25.3) |
| RP-11-113m14 (10q26.13) | RP-11-70E19 (10q26.12) |
| RP-11-10P15 (10126.13) | RP-11-506P9 (10q25.3) |

Figure 13:
FIG. 13 top panel shows agarose electrophoresis of DOP-PCR-amplified BAC's DNA. The origins of samples are indicated above each lane: 1 (RP-11-265k23), 2 (RP-11-849), 3 (RP-11-354m20), 4 (RP-11-280F22), 5 (RP-11-113m14), 6 (RP-11-70E19), 7 (RP-11-10P15), and 8 (RP-11-506P9). DNA markers were SPP-1/EcoRI ($M_1$) and pUC19/HpaII ($M_2$).
Figure 13:
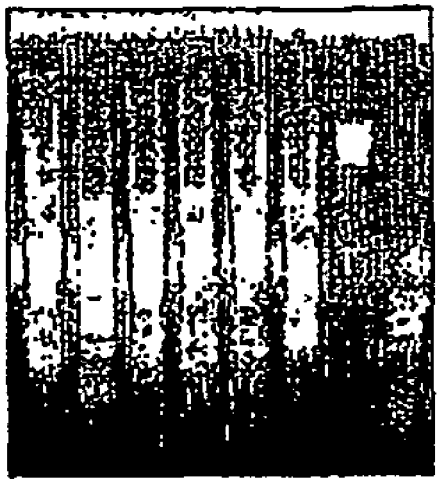
Figure 13:

Dilution of source BAC DNAs and amplification by DOP-PCR 100 ng of each diluted BAC's DNA was amplified using one round of conventional DOP-PCR (Telenius, 1992) and 5 ul of each amplified products was run on a 1% Agarose gel and the rest of products were purified and eluted into 50 μl of Ultrapure Water by use of a PCR purification Sit. As shown in FIG. 13, except for RP-11-849 (1711.2), all the other 7 BAC DNA probes were successfully amplified by DOP-PCR.
Preparation of Depleted BAC's DNA for Array Printing:

25 μg of Human Cot-1 DNA (Cat. No., 15279-011, invitrogen) was labelled by biotin-16-dUTP (Cat. No., 1,093 070, Roche) through a nick-translation kit (Cat. No., 976 776) and purified using Ultrapure PCR purification kits (Cat. No., 12500-250, Mo Bio Laboratories Inc. USA) according to manufacture's instructions, followed by precipitation using 0.1 volume of 3 M NaAc (pH 5.2) and 2 volumes of 100% cold Ethanol, dried in an Oven at 60° C., and resuspended in 100 μl of TE buffer.

4.4 mg (440 μl) streptavidin magnetic particles were prepared according to the Manufacture's instructions and resuspended in 125 μl of 10 mM TRIS-HCl, pH 8.0, 1 mM EDTA, pH 8.0, 2 M NaCl (2× binding and washing buffer).

125 μl of prepared streptavidin magnetic particles was mixed with 100 μl of biotinylated Cot-1 DNA and incubated at room temperature for 40 min with axial rotation. Tubas were then applied to a magnetic particle separator for 10 min.

Non-bound Cot-1 DNA was removed by washing the beads 3-fold in 0.1×SSC, 0.1% SDS at room temperature, followed by three washes in 0.1×SSC, 0.1% SDS at 65° C. The beads was resuspended into 100 μl of 6×SSC, 0.1% SDS.

1 μg of each of 5q25 BAC's DNA and 10q25-26 mixed 6 BAC DNA was precipitated using ⅒ volume of 3 M NaAC (pH 5.2) and 2 volumes of cold 100% ethanol, dried in an Oven at 65° C. and resuspended into 100 μl of 6×SSC, 0.1% SDS.

100 μl of prepared beads and 100 μl of each of source BAC's DNAs were mixed together, denatured by boiling for 10 min, and hybridised at 65° C. overnight.

Tubes were then applied to a magnetic particle separator for 3 min, and the supernatant was gently removed and purified using a Ultrapure PCR purification kits according to the manufacturer's instructions, and resuspended into 50 μl TE buffer (10 mM TRIS-HCl, pH 8.0, 0.1 mM EDTA, pH 8.0).

5 μl of eluted products were subjected to $CAT_4DOP$-PCR amplification (Craig, 1997). 5 ul of each product was checked on a 1% Agarose gel (FIG. 13 bottom panel) and the rest was purified, eluted into 50 μl of Ultrapure water. and spotted onto a chip as previously described.

EXAMPLE 17

Preparation of SEP-PCR Probes for Array Printing
(i) Y Chromosome-Specific Sequences
10 different DYS loci were selected:

| | |
|---|---|
| DYS19 (3682 bp) | DYS385 (4676 bp) |
| DYS389 (4244 bp) | DYS390 (3872 bp) |
| DYS391 (4039 bp) | DYS392 (3252 bp) |
| DYS393 (3454 bp) | DYS437 (3043 bp) |
| DYS438 (3010 bp) | DYS439 (2054 bp) |

(ii) Source of a Male Genomic DNA Sample

Figure 14:
FIG. 14 top panel shows agarose electrophoresis of Expanded Long Template PCR-amplified products. The origins of samples are indicated above each lane. DNA markers was SPP-1/EcoRI ($M_1$).
Figure 14:
Figure 14:
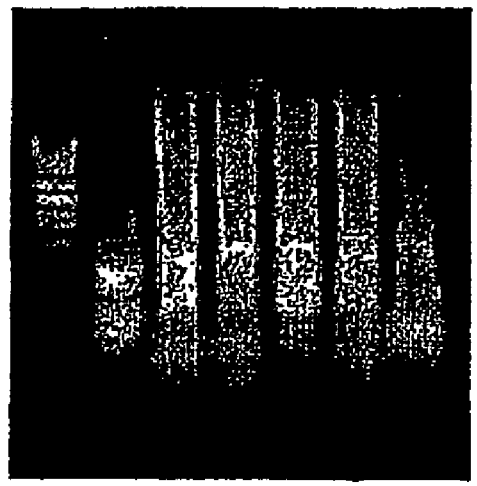

DNA primarily from lymphocyte preps using Qiagen kit-standard protocol was pooled from more than 10 different samples of normal male, including different nationalities such as Asian, Caucasian, and Greek, and so on. To make the pooled male DNA, 10 μl of each sample was mixed together.
(ii) Expanded Long Template PCR (ELT-PCR) Amplification PCR was carried out using Expanded Long Template PCR System (Cat. No. 1681 842, Roche) according to the manufacturers instructions in a total volume of 50 μl for each locus, Only seven out of 10 DYS loci were successfully amplified, and 10 μl of each amplified product was run on a 1% Agarose gel as shown in FIG. 14 top panel. These amplified products were termed S1-S7, including S1 (DYS19), S2 (DYS385), S3 (DYS 389), S4 (DYS 390), S5 (DYS 437), S6 (DYS439), and S7 (DYS 393). Samples of S1, S2, S3, and S4 were pooled together and termed SP1. Sequences of primers used to amplify these 10 different DYS loci are listed in Table 5.
(iii) DOP-PCR Using ELT-PCR Amplified Products 1 μl of each of four DYS loci-specific ELT-PCR amplified products (DYS17, DYS385, DYS389, and DYS390) was further subjected to another round of DOP-PCR amplification. 5 μl of each amplified product was run on 1% Agarose gel as shown in FIG. 14 bottom panel, and the rest was purified using a ultrapure purification kit and stored at −20° C. These amplified products were termed SD1-SD4, including SD1 (DYS19), SD2 (DYS385), SD3 (DYS 389), and SD4 (DYS 390). Samples of SD1, SD2, SD3, and SD4 were pooled together 10 and termed SPD1.

TABLE 5

Primers used for amplification of 10 different
DYS loci for both the preparation of probes
for array printing and the preparation of
single-cell targets for array CGH analyses
using Selectively-Enhanced Primer-extension-
preamplification (SEP)

| Locus | Orientation | Primer sequences (5'→3') | Products (bp) |
|---|---|---|---|
| DYS19 | F | ATGTGGGCGATCCTATT (SEQ ID NO. 6) | 3682 |
| | R | TTGACAAGCCCAAAGTT (SEQ ID NO. 7) | |

TABLE 5-continued

Primers used for amplification of 10 different DYS loci for both the preparation of probes for array printing and the preparation of single-cell targets for array CGH analyses using Selectively-Enhanced Primer-extension-preamplification (SEP)

| Locus | Orientation | Primer sequences (5'→3') | Products (bp) |
|---|---|---|---|
| DYS385 | F | TGAGTCGTTTAGAGGGCTTCC (SEQ ID NO. 8) | 4676 |
|  | R | AATCTACGGGCCACGCAT (SEQ ID NO. 9) |  |
| DYS389 | F | TCCTAGGGATTAGGCCTTCAGTA (SEQ ID NO. 10) | 4244 |
|  | R | TGCATTAGCATGAGAGATCCTG (SEQ ID NO. 11) |  |
| DYS390 | F | TGGTTCTAAATGAGGCCGAGG (SEQ ID NO. 12) | 3872 |
|  | R | TCGCTATGTGGGCCAGTCT (SEQ ID NO. 13) |  |
| DYS391 | F | TTTTTGACAATAGCCATTCCAG (SEQ ID NO. 14) | 4039 |
|  | R | ACCAACATTTTCATACTAAGATAGGG (SEQ ID NO. 15) |  |
| DYS392 | F | TTACAATTGAGAAACGGCTCCTG (SEQ ID NO. 16) | 3252 |
|  | R | TGGAGGCATCACACTACCTGAC (SEQ ID NO. 17) |  |
| DYS393 | F | CATCTCCCAGGTTCAAGTGATTC (SEQ ID NO. 18) | 3454 |
|  | R | TTCGCACCAACATTCTCCATTCTG (SEQ ID NO. 19) |  |
| DYS437 | F | AATGCACTCAGAGGACTGGACC (SEQ ID NO. 20) | 3043 |
|  | R | TGGAACCTATCTCCTGTTCATGTG (SEQ ID NO. 21) |  |
| DYS438 | F | CTCGGACTCCTGACATCAAGTG (SEQ ID NO. 22) | 3153 |
|  | R | GAAACCGTGCATCTAACACCAG (SEQ ID NO. 23) |  |
| DYS439 | F | GCTCAGAGTCATGGTTTCCAGC (SEQ ID NO. 24) | 2054 |
|  | R | GCTGCATAAAGTGTCACAGAGCC (SEQ ID NO. 25) |  |

EXAMPLE 18

Preparation of Cy3- and Cy5dUTP-Labelled Targets for Array CGH Analyses Using SEP-PCR Technology
(i) Y Chromosome-Specific Sequences for SEP Amplification 7 different DYS loci were selected:

| DYS19 (3682 bp) | DYS385 (4676 bp) |
|---|---|
| DYS389 (4244 bp) | DYS390 (3872 bp) |
| DYS393 (3454 bp) | DYS437 (3043 bp) |
| DYS439 (2054 bp) |  |

(ii) Strategies of SEP Amplification

Single-cell DOP-PCR was carried out described previously, except that different combinations of DYS primers were added to the $1^{st}$ and $2^{nd}$ rounds of DOP-PCR, including $1^{st}$ combination: 1 μl of pooled primers (0.1 p mol, F-primers only) in both $1^{st}$ and $2^{nd}$ rounds of DOP-PCR $2^{nd}$ combination: 1 μl of pooled primers (0.1 p mol, F- and R-primer) in both $1^{st}$ and $2^{nd}$ rounds of DOP-PCR $3^{rd}$ combination: 1 μl of pooled primers (0.01 p mol, F-primer) in both $1^{st}$ and $2^{nd}$ rounds of DOP-PCR $4^{th}$ combination: 1 μl of pooled primers (0.01 p mol, F- and R-primer) in both $1^{st}$ and $2^{nd}$ rounds of DOP-PCR 4 single female cells (FIG. 15 top panel) and 4 single male cells (FIG. 15 bottom panel) were separately amplified using each of the above four conditions. 5 μl of each amplified product was run on a 1% Agarose gel as shown in FIG. 15, and the rest was purified using a Ultrapure PCR purification kit.

Finally, it will be appreciated that various modifications and variations of the methods and compositions of the invention described herein will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the fields of the detection of chromosome abnormalities, prenatal diagnosis and preimplantation genetic diagnosis, molecular biology or related fields are intended to be within the scope of the present invention.

The invention claimed is:

1. A method of comparing at least one chromosome or part thereof from a cell with a first karyotype with the corresponding chromosome or part thereof from a cell with a second karyotype, the method including the steps of:
 (a) randomly amplifying DNA from an isolated chromosome or part of an isolated chromosome, the amplified DNA being depleted of repetitive sequences and/or sequences that are over represented due to the random amplification;
 (b) attaching the amplified DNA to a solid substrate;
 (c) amplifying DNA from one or more cells with a first karyotype and amplifying DNA from one or more cells with a second karyotype;
 (d) labelling the amplified DNA from the one or more cells with a first karyotype with a first label, and labelling the amplified DNA from the one or more cells with a second karyotype with a second label, wherein the first and second labels are detectably different;
 (e) hybridizing the amplified and labelled DNA from the one or more cells with a first karyotype to the amplified DNA attached to the solid substrate, and hybridizing the amplified and labelled DNA from the one or more cells with a second karyotype to the amplified DNA attached to the solid substrate; and
 (f) comparing the relative amount of first and second labels hybridized to the amplified DNA attached to the solid substrate.

2. The method of claim 1, wherein the part of an isolated chromosome is a cloned fragment of a chromosome.

3. The method of claim 1 or 2, wherein the repetitive sequences include one or more repetitive sequences selected from the group consisting of: Cot-1 sequences, simple repeated DNA, satellite repeats, mini-satellite repeats, chromosome-specific repeats, micro-satellite repeats, repeated genes, sequences derived from transposable elements, elements derived from multiple copies of viruses such as retroviruses, repeats associated with centromeres or telomeres, and repeats associated with heterochromatin.

4. The method of claim 1, wherein the amplifying of DNA from one or more cells with a first karyotype and the amplifying of DNA from one or more cells with a second karyotype is randomly primed amplification.

5. The method of claim 1, wherein the amplified DNA from one or more cells with a first karyotype is DNA amplified from 1 to 20 cells.

6. The method of claim 1, wherein the amplifying DNA from one or more cells with a first karyotype and amplifying DNA from one or more cells with a second karyotype includes randomly amplifying DNA from 100 or less cells with a first karyotype and randomly amplifying DNA from one or more cells with a second karyotype.

7. The method of claim 1, wherein the amplifying DNA from one or more cells with a first karyotype and amplifying DNA from one or more cells with a second karyotype includes randomly amplifying DNA from a single cell with a first karyotype and randomly amplifying DNA from one or more cells with a second karyotype.

* * * * *